United States Patent
Masuzawa et al.

(10) Patent No.: US 8,632,449 B2
(45) Date of Patent: Jan. 21, 2014

(54) HEART PUMP CONTROLLER

(75) Inventors: Toru Masuzawa, Hitachi (JP); Eisuke Sasaki, Ibaraki (JP); Daniel Timms, Ferny Hills (AU)

(73) Assignee: BiVACOR Pty Ltd, Wilston QLD (AU)

( * ) Notice: Subject to any disclaimer, the term of this patent is extended or adjusted under 35 U.S.C. 154(b) by 0 days.

(21) Appl. No.: 13/264,747

(22) PCT Filed: Apr. 16, 2010

(86) PCT No.: PCT/AU2010/000428
§ 371 (c)(1),
(2), (4) Date: Jun. 1, 2012

(87) PCT Pub. No.: WO2010/118475
PCT Pub. Date: Oct. 21, 2010

(65) Prior Publication Data
US 2012/0245680 A1    Sep. 27, 2012

(30) Foreign Application Priority Data

Apr. 16, 2009  (AU) ................. 2009901620
May 8, 2009  (JP) ................. 2009-113579

(51) Int. Cl.
*A61M 1/12*    (2006.01)
(52) U.S. Cl.
USPC .......................... 600/17; 623/3.14
(58) Field of Classification Search
USPC .......................... 600/17; 623/3.14
See application file for complete search history.

(56) References Cited

U.S. PATENT DOCUMENTS

| 2,700,343 | A | 1/1955 | Pezzillo |
| 4,589,822 | A | 5/1986 | Clausen et al. |

(Continued)

FOREIGN PATENT DOCUMENTS

| CA | 2638958 | 11/2011 |
| EP | 1065383 A1 | 1/2001 |

(Continued)

OTHER PUBLICATIONS

Greatrex, Nicholas A et al, "Axial Magnetic Bearing Development for the BiVACOR Rotary BiVAD/TAH", IEEE Transactions on Biomedical Engineering, vol. 57, No. 3, Mar. 2010, pp. 714-721; Abstract; Last paragraph on p. 714; Magnetic Bearing Design (pp. 715-716); Levitation Performance and Stability (p. 717); Discussion (pp. 719-720); Conclusion (p. 720); Figures 1-3.

(Continued)

*Primary Examiner* — Christopher Koharski
*Assistant Examiner* — Michael Carey
(74) *Attorney, Agent, or Firm* — Hahn & Voight PLLC; Roger C. Hahn

(57) ABSTRACT

A heart pump including first and second cavities, each cavity including a respective inlet and outlet, a connecting tube extending between the first and second cavities, an impeller including: a first set of vanes mounted on a first rotor in the first cavity portion; a second set of vanes mounted on a second rotor in the second cavity portion; and, a shaft connecting the first and second rotors, the shaft extending through the connecting tube, a drive for rotating the impeller and a magnetic bearing including at least one bearing coil for controlling an axial position of the impeller, at least one of the drive and magnetic bearing being mounted outwardly of the connecting tube, at least partially between the first and second cavity portions.

34 Claims, 24 Drawing Sheets

(56) References Cited

U.S. PATENT DOCUMENTS

| | | |
|---|---|---|
| 5,195,877 A | 3/1993 | Kletschka |
| 5,601,418 A | 2/1997 | Ohara et al. |
| 5,725,357 A | 3/1998 | Nakazeki et al. |
| 5,890,883 A | 4/1999 | Golding et al. |
| 5,928,131 A | 7/1999 | Prem |
| 6,179,773 B1 | 1/2001 | Prem et al. |
| 6,220,832 B1 | 4/2001 | Schob |
| 6,227,797 B1 | 5/2001 | Watterson et al. |
| 6,293,901 B1 | 9/2001 | Prem |
| 6,351,048 B1 | 2/2002 | Schob et al. |
| 6,394,769 B1 | 5/2002 | Bearnson et al. |
| 6,422,838 B1 * | 7/2002 | Sloteman .................. 417/423.5 |
| 6,527,698 B1 | 3/2003 | Kung et al. |
| 6,575,717 B2 | 6/2003 | Ozaki et al. |
| 6,688,861 B2 | 2/2004 | Wampler |
| 6,717,311 B2 | 4/2004 | Locke |
| 2002/0109621 A1 | 8/2002 | Khair et al. |
| 2004/0267344 A1 | 12/2004 | Stett et al. |
| 2005/0214131 A1 | 9/2005 | Miles et al. |
| 2007/0253842 A1 | 11/2007 | Horvath et al. |
| 2011/0118619 A1 | 5/2011 | Burton et al. |

FOREIGN PATENT DOCUMENTS

| | | |
|---|---|---|
| JP | 7255834 A | 10/1995 |
| JP | 2001061957 A | 3/2001 |
| JP | 2001-224568 A | 8/2001 |
| JP | 2003-230547 A | 8/2003 |
| JP | 2004-61251 A | 2/2004 |
| JP | 3930834 | 6/2007 |
| WO | 02-053028 A2 | 7/2002 |
| WO | 2004-032738 A1 | 4/2004 |
| WO | 2004-043252 A1 | 5/2004 |
| WO | 2004-047636 A1 | 6/2004 |
| WO | 2004-098389 A2 | 11/2004 |
| WO | 2004098677 A1 | 11/2004 |
| WO | WO 2004098677 A1 * | 11/2004 |
| WO | 2006053384 A1 | 5/2006 |
| WO | 2007-056493 A1 | 5/2007 |

OTHER PUBLICATIONS

Maslen E. et al., "Feedback Control Applications in Artificial Hearts", 1998 IEEE Control Systems Magazine, vol. 18(6), pp. 26-34.

* cited by examiner

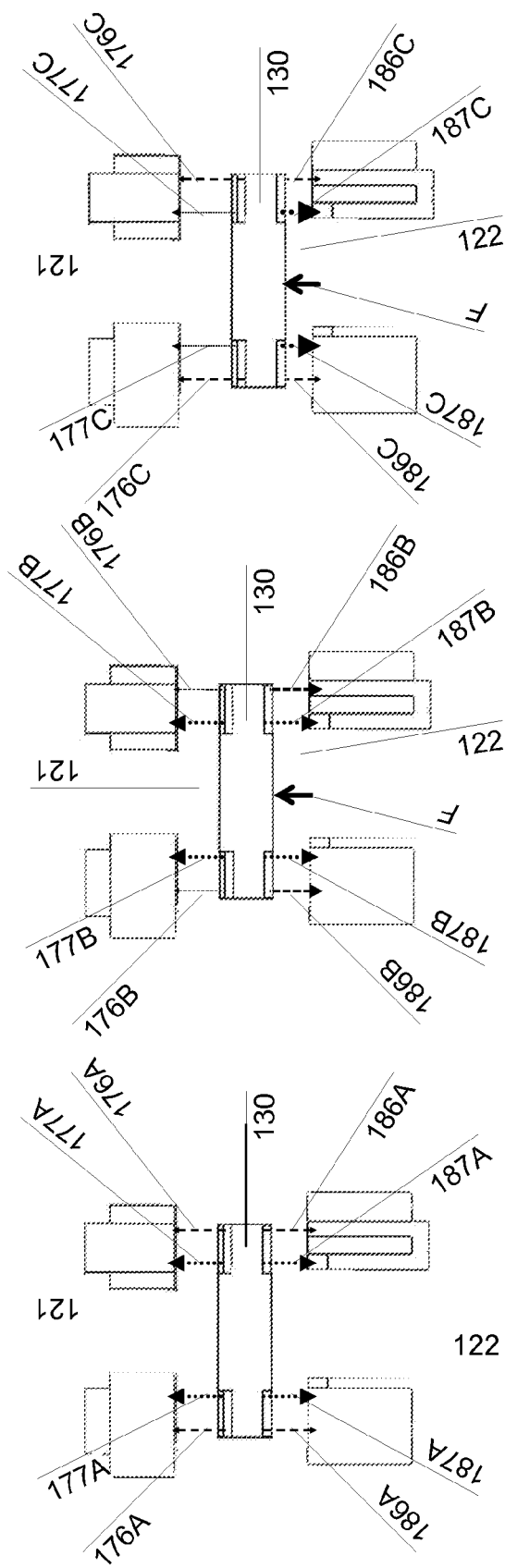

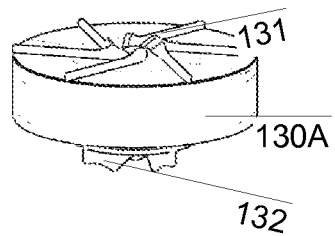
Fig. 16D
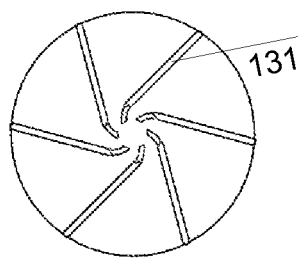 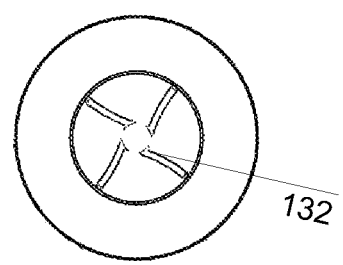
Fig. 16E          Fig. 16F

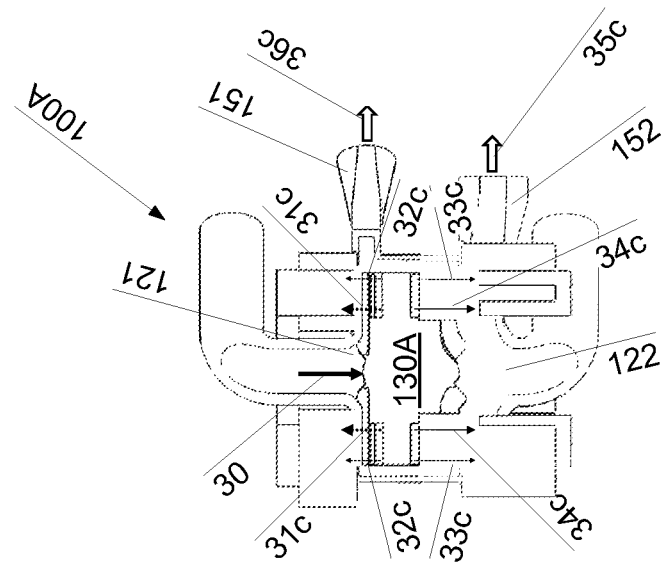
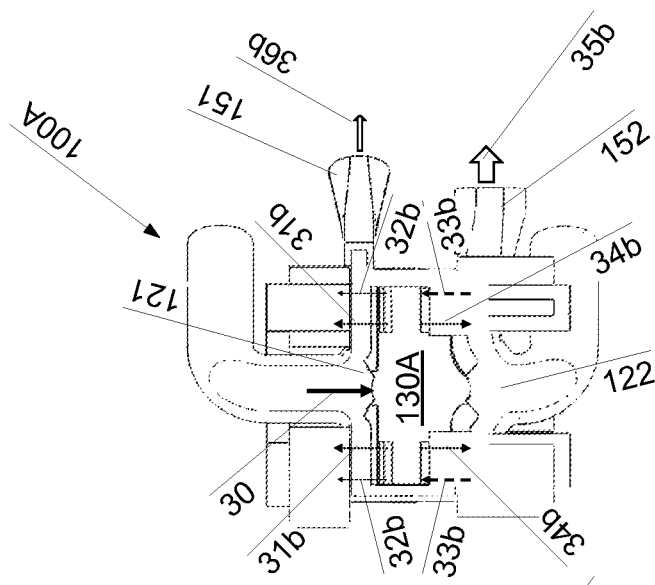
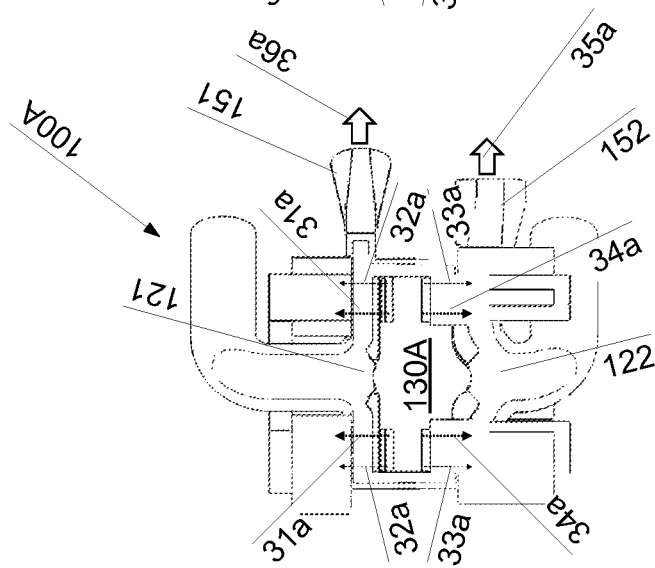

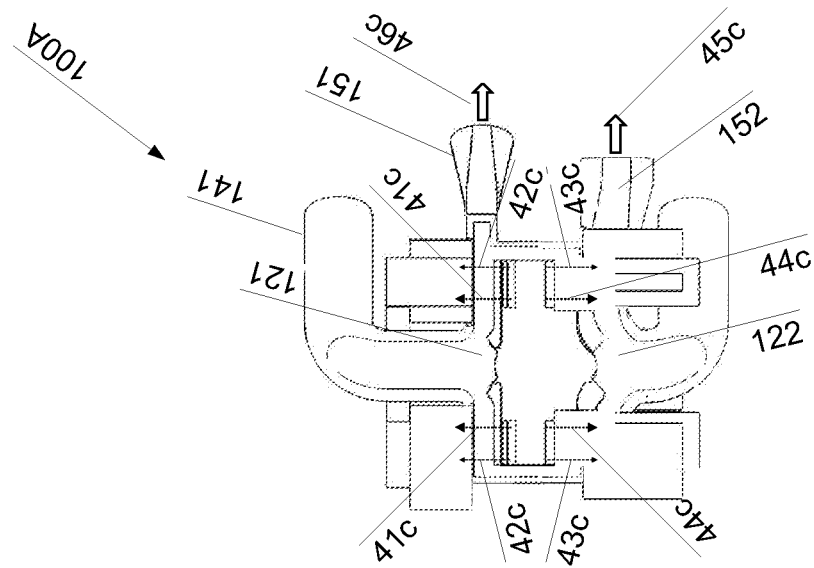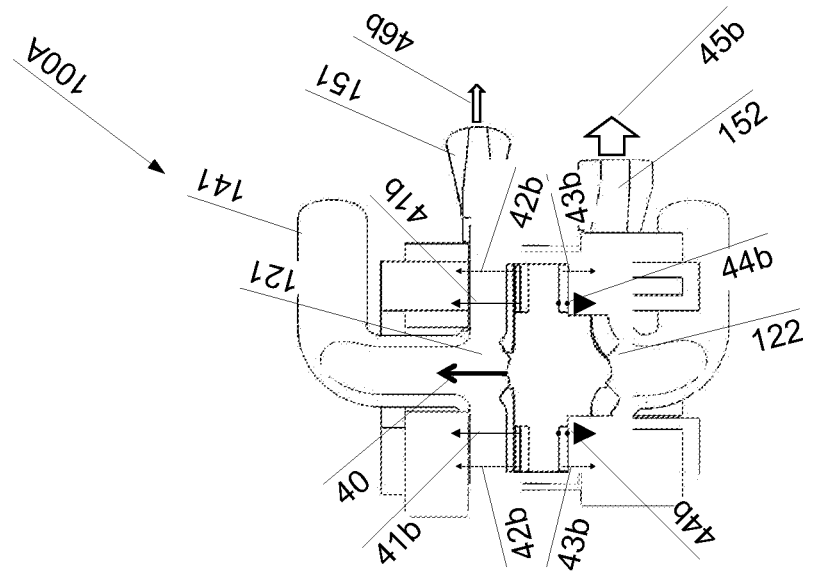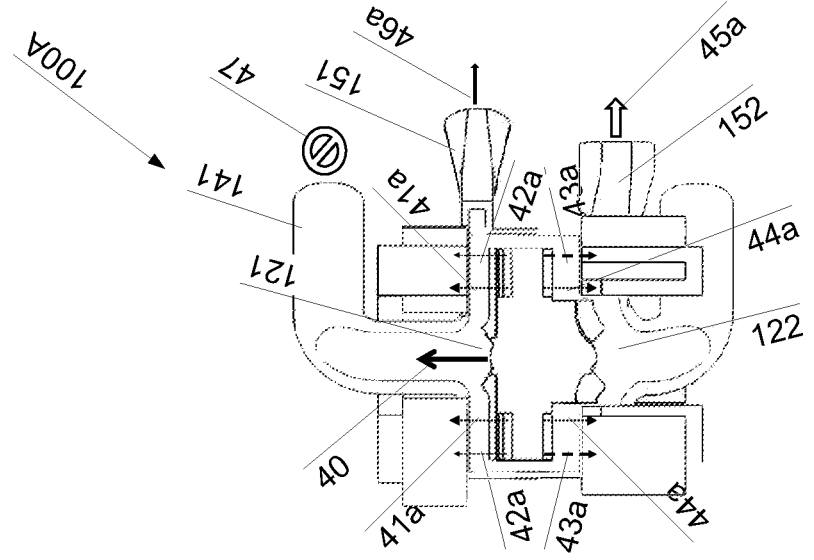

Fig. 20A
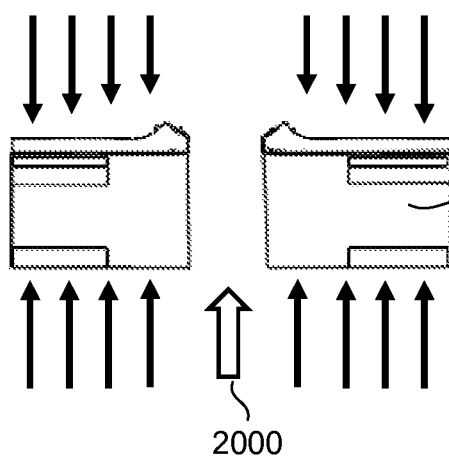
Fig. 20B
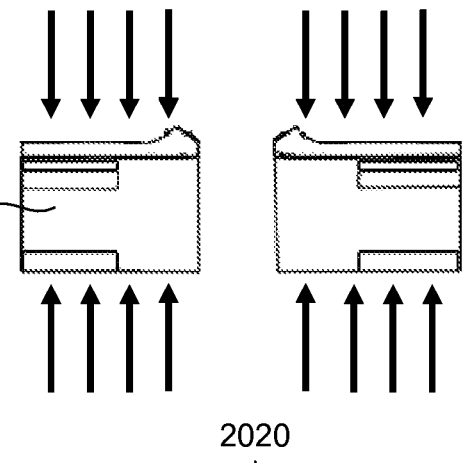
Fig. 20C
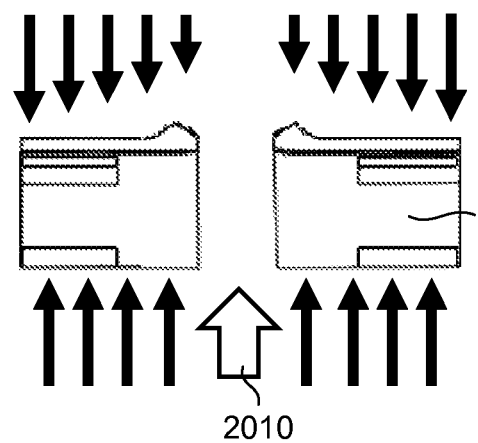
Fig. 20D

HEART PUMP CONTROLLER

BACKGROUND OF THE INVENTION

The present invention relates to a controller for a heart pump and method of controlling a heart pump.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

The use of mechanical device therapy to treat heart failure is increasing as the general population ages and the number of donor organs for heart transplantation remains limited. Devices can be used to bridge a patient to heart trans-plant, to recovery, or indeed as a destination alternative. The latter support strategy requires a device with increased mechanical durability/lifetime.

A blood pump used for an artificial heart apparatus is required to be compact and have a simple structure and centrifugal pumps or similar are therefore typically used. In addition, the blood pump must be a pump that can continue to rotate without any trouble over a long time. A contactless rotor using a magnetic bearing apparatus is suitable for such a pump apparatus.

Japanese Patent Publication No. 3930834 describes a pump apparatus configured by the following: a circular upper permanent magnet is provided on a top surface of a rotor as a rotating device for a centrifugal pump having a magnetic bearing apparatus; at an upper stator located above the rotor is provided suction electromagnetic means that cooperates with the circular upper permanent magnet to generate a suction force with respect to the rotor in an axial direction; a plurality of lower permanent magnets for rotating the rotor are provided on a bottom surface of the rotor; and at a lower stator located under the rotor is provided rotation electromagnetic means that cooperates with the permanent magnets for rotating the rotor to perform rotational movement of the rotor.

The human heart has a left ventricle and a right ventricle, and the left ventricle pumps blood through a body, while the right ventricle pumps blood to lungs for re-oxygenation.

In addition, it is necessary to control the blood pumps so that a discharge amount from the left ventricle blood pump becomes different than that from the right ventricle blood pump, but since only one pump chamber is provided in the pump using the rotating device disclosed in Japanese Patent Publication No. 3930834, two separate pumps, one pump for pumping blood through the body and the other pump for pumping blood to the lungs, are required when applying to the above-described blood pump, and thus there are problems that a pump apparatus becomes large and complicated, making it unsuitable for implantation in a subject.

Mechanical durability is dependent on the functionality of the device, in particular, the type of bearings implemented. First generation pulsatile devices necessitate contacting components, which limits their predicted mechanical lifetime below three years. The reduced size of second generation non-pulsatile rotary impeller devices has accelerated them to the forefront of VAD development.

However, initial techniques for impeller support also imposed significant limitations on device lifetime, as they required a shaft, seals and bearings U.S. Pat. No. 4,589,822. Subsequent improvements resulted in devices that rely on blood immersed pivot support U.S. Pat. No. 5,601,418; however predicted service life is still below five years.

Several techniques have since been developed to improve device lifetime, ranging from complete magnetic suspension U.S. Pat. No. 6,575,717, to passive hydrodynamic suspension U.S. Pat. No. 6,227,797. These third generation devices eliminate contact wear and reduce the number of moving components, potentially increasing lifetime to beyond ten years. These latest generation suspension techniques eliminate any point to point contact which may also improve the hemolytic performance of the pump.

A number of commercial devices, as well as research devices implement hydrodynamic or magnetic bearing technology. For example, both the Ventrassist (Ventracor, Sydney, NSW, AU) and the HVAD (Heatware, Framingham, Mass., USA) incorporate an impeller that is completely suspended with hydrodynamic forces and driven with an electromagnetic motor U.S. Pat. No. 6,227,797 and U.S. Pat. No. 6,688,861 respectively. The Duraheart (Terumo, Ann Arbor, Mich., USA) uses an axial magnetic bearing with a permanent magnetic coupling motor U.S. Pat. No. 6,575,717. Heartmate III (Thoratec, Woburn, Mass., USA) uses a combined radial self-bearing motor U.S. Pat. No. 6,351,048 while the Levacor (formerly Heartquest, Worldheart, Ottawa, ON, Canada) uses an axial magnetic bearing and electromagnetically coupled motor U.S. Pat. No. 6,394,769.

All of the devices mentioned provide left ventricular assistance (LVAD). However, a significant number of patients also require a device for right ventricular assistance (RVAD). The incidence of bi-ventricular failure is not always initially apparent in heart failure patients, and right ventricular heart failure may develop in up to 40% of patients receiving LVAD assistance.

One of the most successful BiVAD techniques used in clinical practice uses the extracorporeal connection of two Thoratec PVA devices. Smaller second and third generation rotary systems have also been proposed which make use of two separate rotary pumps, such as the combined Coraide and Dexaide U.S. Pat. No. 5,890,883 and two Gyro pumps U.S. Pat. No. 5,601,418.

However, all currently available bi-ventricular assist systems require the use of two devices, with separate controllers, which can introduce left and right outflow control issues, particularly with the second and third generation devices. The dual device approach also increases implantation size as well as the cost of the therapy.

Single rotary pumps have also been designed to augment the function of both ventricles of a failing heart, as described in U.S. Pat. No. 5,725,357, U.S. Pat. No. 6,220,832, WO2004098677 and WO2006053384A1. Each of these devices include a double sided impeller that rotates at a common speed, with each side of the impeller respectively configured for left and right heart assistance. This effectively introduces an inherent problem regarding the ability to independently control and thus balance the outflow from the left and right sides of the device, i.e. an increase in impeller rotational speed with produce a corresponding increase in outflow from both cavities.

WO2006053384A1 addressed this issue by introducing the ability to axially displace the rotating impeller within the cavity so as to simultaneously alter the relative efficiencies of each side of the device. However, this application describes the control method used to achieve this axial displacement as active, thus requiring the use of feedback signals from pressure sensors and the like to actively control and maintain a desired set axial location. This method of control would inherently consume excessive amounts of electrical power.

The ability to maintain a balance between the left and right outflow of a BiVAD system is essential for successful device operation. Haemodynamic parameters that may upset this balance include the bronchial flow, relative changes in systemic and pulmonary vascular resistance, relative changes in left and right ventricular contractility, pulmonic or systemic congestion, and ventricular collapse. These conditions infer that a technique for balancing the left and right VAD hydraulic output is required for long term support.

To operate and control the hydraulic output from each blood pump, parameters such as motor power, speed, differential pressure (inlet-outlet) and flow are required. Whilst determining the motor power and speed is relatively easy, detecting the remaining parameters conventionally requires additional instrumentation, such as pressure sensors and flow meters. These components increase the possibility of device failure; as such components have limited long term reliability. Furthermore, their addition to the device can induce extra blood contact with other foreign material, exacerbating the potential for blood damage.

Previous attempts to regulate the outflow from each device and balance the left/right outflow requirements have often relied on the use of a pressure sensor to detect left atrial pressure (LAP). A feedback mechanism is then employed to either reduce LVAD speed, or increase RVAD speed, in the presence of reduced LAP. Another technique includes the surgical introduction of a shunt between the left and right atrium to safely protect against the potentially disastrous build up of fluid in either atrium. Alternatively, U.S. Pat. No. 6,527,698 includes a conduit linking right to left atria through which flow is varied via a variable occluding valve. However, this technique introduces an additional blood contacting conduit, as well as complexities involved with active feedback control, such as the need for sensors. Furthermore, this solution can help to balance the fluid distribution but does not provide a method for controlling the alteration of device outflow.

As mentioned, the ability to alter the left and right outflow of a BiVAD is important, especially in the post operative period when the neuro-humoral auto regulatory mechanisms are least partially ablated by anaesthesia and critical illness.

Many control algorithms exist for the active levitation of magnetic bearing systems. While most focus on the maintenance of a centralised rotor position, an alternative technique exists which focuses on the minimisation of power consumption. The latter controller uses passively generated forces from permanent magnets within the magnetic circuit to counteract external forces which would otherwise require power from the electromagnetic coils. This results in movement of the impeller from the centralised position, until an equilibrium of external and permanent magnetic forces is reached. Therefore, the power consumption of the active electromagnetic coils is returned to a minimal state. A number of rotary blood pump designs implement this form of zero power control.

Masuzawa et. al. (2004) implemented zero power control in a reluctance type radial magnetic motor bearing to completely suspend the rotor of a centrifugal blood pump. The system places the magnetic material concentrically around the rotor, and includes permanent magnets to provide additional bias flux to the magnetic circuit. These magnets are used by the zero power controller to reduce power consumption when compared to a central position controller. During operation, the application of a radial hydraulic force to the rotor causes a translation of this rotor in a direction perpendicular to the axis of rotation, and opposite to the applied force. However, no significant effect on pump outflow can be observed with this motion, as altering radial clearance gaps has minimal effect on hydraulic efficiency. (Masuzawa, T., H. Onuma, and Y. Okada, Zero Power Control for Magnetically Suspended Artificial Heart. Jido Seigyo Rengo Koenkai Koen Ronbunshu, 2004. 47: p. 322).

U.S. Pat. No. 6,717,311 suspends the rotor of a centrifugal blood pump in the axial direction with a lorentz type magnetic bearing system. This system again places the magnetic material concentrically around the rotor, however the magnetic forces act perpendicularly to the pole face, in the direction parallel to the rotational axis. Additional permanent magnets, not included in the magnetic bearing circuit, are configured to provide a counteracting force when an axial hydraulic force is encountered. This counteracting force is effective when allowing the zero power controller to translate the impeller in the same direction as the applied force. Whilst this motion can be adapted to alter the outflow of the device, motion in the same direction as the applied force is undesirable, and will, for example, increase outflow when a decrease is warranted.

U.S. Pat. No. 6,293,901 uses a lorentz type axial magnetic bearing, also concentrically located around the rotor. Suspension in the radial direction is achieved using a configuration of repelling permanent magnets (U.S. Pat. No. 5,928,131, U.S. Pat. No. 6,179,773) configured in a halbach array (U.S. Pat. No. 6,293,901). These magnets are used to achieve zero power control, which relocates the axial position of the impeller in response to hydraulic axial forces. Since this configuration uses repelling magnets to achieve this, their low stiffness may not provide sufficient counteraction of force for a given displacement. Although axial relocation is opposite to the direction of the applied force, the shrouded configuration as well as the location of the impeller vanes beneath the impeller does not provide for a reduction in pump outflow in response to the forces generated during instances of ventricular collapse. Therefore, the zero power controller can minimise bearing bower, but not provide flow control based on changing preload conditions. Furthermore, the mentioned axial gap between the bottom impeller shroud and casing (0.005 inch) is too small, and impeller blade height too large, to produce an appreciable change in hydraulic performance with the maximum axial translation possible, even if the shroud was semi-open.

US 2007253842 describes a pump includes a housing, a stator supported in the housing, and a rotor assembly. The rotor assembly includes a rotor supported in the housing for rotation relative to the stator about an axis. The rotor assembly also includes a first impeller operatively coupled to a first axial end of the rotor for rotation with the rotor about the axis. The rotor assembly further includes a second impeller operatively coupled to a second axial end of the rotor, opposite the first axial end, for rotation with the rotor about the axis. The rotor assembly is movable along the axis relative to the housing to adjust hydraulic performance characteristics of the pump.

SUMMARY OF THE PRESENT INVENTION

The present invention seeks to substantially overcome, or at least ameliorate, one or more disadvantages of existing arrangements.

In a first broad form the present invention seeks to provide a heart pump including:
   a) first and second cavity portions, each cavity portion including a respective inlet and outlet;

b) a connecting tube extending between the first and second cavity portion;
c) an impeller including:
  i) a first set of vanes mounted on a first rotor in the first cavity portions;
  ii) a second set of vanes mounted on a second rotor in the second cavity portion; and,
  iii) a shaft connecting the first and second rotors, the shaft extending through the connecting tube;
d) a drive for rotating the impeller; and,
e) a magnetic bearing including at least one bearing coil for controlling an axial position of the impeller, at least one of the drive and magnetic bearing being provided at least partially between the first and second cavity portions.

Typically the axial position determines a separation between each set of vanes and a respective cavity surface, the separation being used to control the fluid flows from the inlets to the outlets.

Typically the drive includes:
a) a second magnetic material provided in the impeller;
b) at least one drive coil that in use generates a magnetic field that cooperates with the second magnetic material allowing the impeller to be rotated.

Typically the second magnetic material includes a number of circumferentially spaced permanent magnets mounted in the impeller, adjacent magnets having opposing polarities.

Typically the second magnetic material is mounted in the second rotor, and wherein the drive is positioned adjacent the second cavity, the drive and second magnetic material being configured to result in an attractive force between the drive and the second rotor.

Typically, in use, the at least one bearing coil generates a magnetic field that cooperates with first magnetic material in the impeller, allowing the axial position of the impeller to be controlled.

Typically the first magnetic material is a permanent magnet.

Typically the at least one bearing coil is for generating a magnetic field that is one of complementary to and counter to the first magnetic field generated by the permanent magnet, thereby controlling the net magnetic field between the bearing and the first magnetic material.

Typically the first magnetic material is mounted in the first rotor and wherein the magnetic bearing is positioned adjacent the first cavity, the magnetic bearing and first magnetic material being configured to result in an attractive force between the magnetic bearing and the first rotor.

Typically the impeller includes:
a) a second magnetic material provided on the second rotor for cooperating with the drive to allow rotation of the impeller; and,
b) a first magnetic material provided on the first rotor for cooperating with the magnetic bearing to allow the axial position of the impeller to be controlled.

Typically:
a) the magnetic bearing is positioned adjacent the first cavity, the magnetic bearing and first rotor being configured to result in a first attractive force between the magnetic bearing and the second rotor; and,
b) the drive is positioned adjacent the second cavity, the drive and second rotor being configured to result in a second attractive force between the drive and the second rotor and wherein the first and second attractive forces are approximately balanced when the impeller is positioned at an approximately axially central position during normal circulatory conditions.

Typically the heart pump includes a controller for:
a) determining movement of the impeller in a first axial direction;
b) causing the magnetic bearing to move the impeller in a second axial direction opposite the first axial direction;
c) determining an indicator indicative of the power used by the magnetic bearing; and,
d) causing the magnetic bearing to control the axial position of the impeller in accordance with the indicator to thereby control a fluid flow between the inlets and the outlets.

Typically the controller is for:
a) comparing the indicator to a threshold; and,
b) causing the magnetic bearing to stop movement of the impeller in the second axial direction depending on the results of the comparison.

Typically the controller is for minimizing the power used by the magnetic bearing.

Typically the controller is for:
a) comparing an axial position of the impeller to position limits; and,
b) controlling the magnetic bearing to maintain the axial position of the impeller within the position limits.

Typically the controller is for:
a) determining a pressure change within at least part of a cavity; and,
b) controlling the axial position of the impeller in response to the pressure change.

Typically the controller is for determining the pressure change by detecting axial movement of the impeller.

Typically the controller is for:
a) detecting movement of the impeller caused by a change in fluid pressure within at least one of the cavity portions; and,
b) causing the magnetic bearing to control the axial position of the impeller to thereby change a fluid flow from the inlet to the outlet for at least one of the cavity portions.

Typically the controller is for, at least one of:
a) causing the magnetic bearing to reduce the separation between the vanes and the cavity surface to thereby increase the flow of fluid from the inlet to the outlet; and,
b) causing the magnetic bearing to increase the separation between the vanes and the cavity surface to thereby decrease the flow of fluid from the inlet to the outlet.

Typically the controller is for:
a) detecting movement of the impeller caused by a change in relative fluid pressures in the cavity portions; and,
b) causing the magnetic bearing to control the axial position of the impeller to thereby alter the relative flow of fluid from the inlets to the outlets.

Typically the controller is for:
a) determining axial movement of the impeller away from a normal balance position;
b) causing the magnetic bearing to move the impeller towards the normal position;
c) monitoring the power used by the magnetic bearing;
d) determining a new balance position in accordance with the power used by the magnetic bearing; and,
e) causing the magnetic bearing to move the impeller to the new balance position.

Typically the normal balance position is used to maintain required fluid flows from each inlet to each outlet.

Typically the new balance position is offset from the normal balance position.

Typically the new balance position is used to adjust relative fluid flows between the inlets and the outlets.

Typically the indicator is determined using an indication of an electrical current used by the magnetic bearing.

Typically the controller is for determining a rate of change of current used by the magnetic bearing to cause axial movement of the impeller.

Typically the controller is for:
a) determining movement of the impeller in a first axial direction;
b) controlling the magnetic bearing to move the impeller in a second axial direction opposite the first axial direction until at least one of:
   i) the power used by the magnetic bearing falls below a predetermined amount; and,
   ii) the axial position of the impeller reaches a position limit.

Typically, the processing system includes:
a) a memory for storing instructions; and,
b) a processor that executes the instructions, thereby causing the processor to:
   i) determine movement of the impeller in the first axial direction;
   ii) generate a signal for causing the magnetic bearing to move the impeller in the second axial direction;
   iii) determine an indicator indicative of the power used by the magnetic bearing; and,
   iv) generate a signal for causing the magnetic bearing to control the axial position of the impeller in accordance with the indicator to thereby control a fluid flow between the inlet and the outlet.

Typically the heat pump includes a controller for:
a) determining movement of an impeller from a balance position within a cavity, the cavity including at least one inlet and at least one outlet, and the impeller including vanes for urging fluid from the inlet to the outlet;
b) causing a magnetic bearing to move the impeller to a new balance position based on an indication of power used by the magnetic bearing, the magnetic bearing including at least one coil for controlling an axial position of the impeller within the cavity, and the new balance position being used to control fluid flow from the inlet to the outlet.

Typically the heat pump includes a controller for controlling an axial position of an impeller within a cavity, a cavity including a first cavity portion having a first inlet and a first outlet and a second cavity portion having a second inlet and a second outlet, and the impeller including first and second sets of vanes, each set of vanes being for urging fluid from a respective inlet to a respective outlet, the controller controlling the axial position such that if the relative pressure in the first cavity increases relative to the second cavity, the impeller is positioned in the first cavity thereby increase the relative fluid flows from the first outlet relative to the second outlet.

Typically the heat pump includes a controller for controlling an axial position of an impeller within a cavity, a cavity including an inlet and an outlet, and the impeller including vanes for urging fluid from the inlet to the outlet, the controller controlling the axial position such that if the pressure in the cavity increases, the impeller is moves away from the inlet, thereby reducing an outlet flow pressure.

In a second broad form the present invention seeks to provide a method of controlling a heart pump, the heart pump including:
a) first and second cavity portions, each cavity portion including a respective inlet and outlet;
b) a connecting tube extending between the first and second cavity portion;
c) an impeller including:
   i) a first set of vanes mounted on a first rotor in the first cavity portions;
   ii) a second set of vanes mounted on a second rotor in the second cavity portion; and,
   iii) a shaft connecting the first and second rotors, the shaft extending through the connecting tube;
d) a drive for rotating the impeller; and,
e) a magnetic bearing including at least one bearing coil for controlling an axial position of the impeller, at least one of the drive and magnetic bearing being provided at least partially between the first and second cavity portions, the method including:
   i) determining movement of the impeller in a first axial direction;
   ii) causing the magnetic bearing to move the impeller in a second axial direction opposite the first axial direction;
   iii) determining an indicator indicative of the power used by the magnetic bearing; and,
   iv) causing the magnetic bearing to control the axial position of the impeller in accordance with the indicator to thereby control a fluid flow between the inlets and the outlets.

In a third broad form the present invention seeks to provide a pump apparatus comprising:
a) a stator;
b) an upper rotor arranged spaced apart above the stator;
c) a lower rotor arranged spaced apart under the stator;
d) connecting means provided rotatably and vertically movable at the stator to connect the upper rotor and the lower rotor;
e) first electromagnetic means that is provided on one surface of the stator opposed to either one of permanent magnets, which are provided on a bottom surface of the upper rotor and a top surface of the lower rotor, cooperates with the permanent magnet, and that generates an acting force with respect to the rotor in an axial direction to thereby levitate the rotor;
f) second electromagnetic means that is provided on the other surface of the stator opposed to the other permanent magnet, and that cooperates with the permanent magnet to thereby rotationally drive the rotor;
g) first pumping means at which a first impeller provided on a top surface of the upper rotor rotates in a first pump chamber; and
h) second pumping means at which a second impeller provided on a bottom surface of the lower rotor rotates in a second pump chamber.

Typically the connecting means is composed of an axis of rotation inserted rotatably and vertically movable into a centre through-hole of the stator.

The pump apparatus may comprise a control section that moves the connecting means forward and backward in an axial direction and that can adjust a gap between the first impeller and an opposed surface of the first pump chamber, and a gap between the second impeller and the pump chamber by coordinating them.

It will be appreciated that the broad forms of the invention may be used individually or in combination.

BRIEF DESCRIPTION OF THE DRAWINGS

An example of the present invention will now be described with reference to the accompanying drawings, in which:—

FIGS. 12A to 12C are schematic side views illustrating the manner in which the impeller position is relocated with zero power control;

FIGS. 16A to 16H are schematic diagrams of an example of a BiVAD;

FIGS. 18A to 18C are schematic diagrams illustrating the adaptation of a BiVAD to alterations in relative vascular resistance;

FIGS. 19A to 19C are schematic diagrams illustrating the adaptation of a BiVAD to heart chamber collapse;

FIGS. 20A to 20D are schematic diagrams illustrating the resultant axial force development on the impeller of a VAD during a variety of common conditions;

DETAILED DESCRIPTION OF THE PREFERRED EMBODIMENTS

Figure 1:
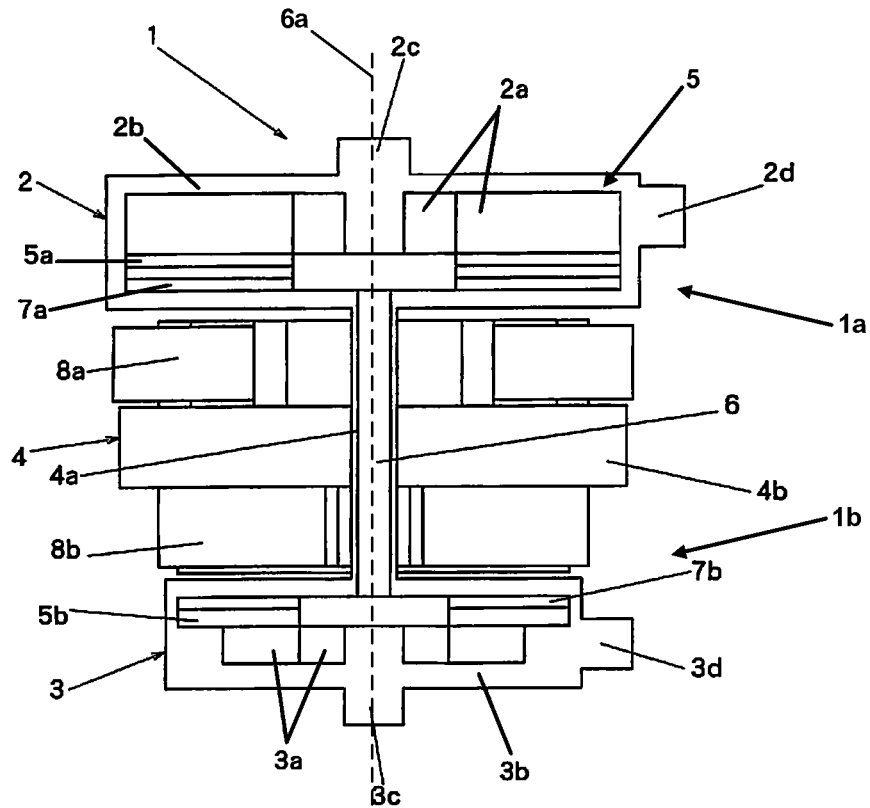
FIG. 1 is a sectional view of an example of a pump apparatus.
Figure 2:
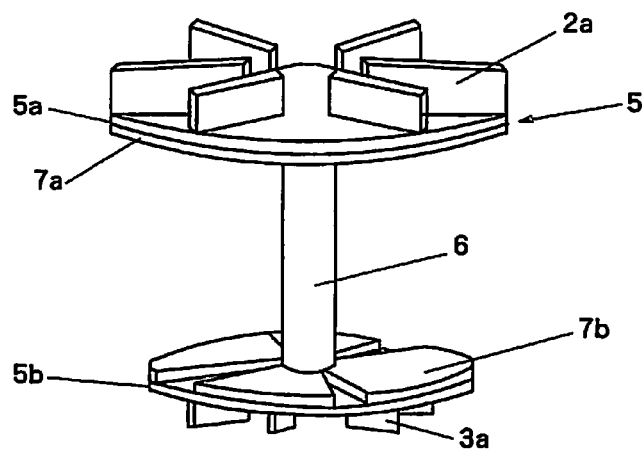
FIG. 2 is a perspective view of an example of the first and second rotors of the pump apparatus of FIG. 1.

A first example of a pump apparatus will now be described with reference to FIGS. 1 to 5. In particular, FIG. 1 is a sectional view of a pump apparatus 1, and FIG. 2 is a perspective view of first and second rotors of the pump apparatus 1.

In this example, a first pump 2 is arranged in a first part 1a of the pump apparatus 1, and a second pump 3 is arranged in a second part 1b of the pump apparatus 1. In this example, at least part of a magnetic bearing and/or a drive, in this example a stator 4, is provided between the first and the second pumps 2, 3.

The pump apparatus includes an impeller 5, having a first rotor 5a and a second rotor 5b arranged in the first and second parts 1a, 1b, with the stator 4 being provided therebetween. The first and second rotors 5a, 5b are connected via a shaft 6 rotatably mounted within the pump apparatus to allow rotation about, and axial movement along an axis 6a in the connecting tube 4a, which in this example extends through the stator 4.

Thus, it will be appreciated that in this example, the connecting tube 4a is provided as a centre-hole through the stator 4, so that the stator 4 is provided radially outwardly of the connecting tube 4a. However, this is not essential and other arrangements can be used. For example, the connecting tube could be annular in shape, with the shaft being a hollow cylinder or a plurality of rods extending through the annular connecting tube.

The first rotor 5a is disk-shaped, and supports a first impeller 2a comprising a plurality of vanes that are provided on a first surface thereof. A first magnetic material in the form of a permanent magnet 7a is provided on a second surface of the first rotor 5a, facing the stator 4. The second rotor 5b is also disk-shaped, and supports a second impeller 3a composed of a plurality of vanes that are provided on a first surface thereof, with a second magnetic material, in the form of a plurality of permanent magnets 7b radially arranged on a second surface thereof, facing the stator 4. The permanent magnets 7b typically include a number of circumferentially spaced permanent magnets mounted in the impeller 5, adjacent magnets having opposing polarities, however, other suitable arrangements may be used, such as a Halbach array.

The stator 4 is composed of a doughnut-shaped body 4b, and first electromagnetic means 8a composed of, for example, four electromagnets, provided on a first surface of the body 4b, facing the first rotor 5a. The first electromagnetic means 8a generates a magnetic field that cooperates with permanent magnet 7a, allowing the axial position of the impeller 5 to be controlled.

Thus, the first electromagnetic means 8a and the first magnetic material form a magnetic bearing including at least one bearing coil for controlling an axial position of the impeller 5. In one example, the at least one bearing coil generates a magnetic field that is one of complementary to and counter to the magnetic field generated by the permanent magnet 7a, thereby controlling the net magnetic field between the bearing and the first magnetic material, allowing the axial position of the first rotor 5a, and hence the impeller 5 to be altered.

In addition, second electromagnetic means 8b is provided on a second surface of the body 4b facing the second rotor 5b that is, for example, composed of twelve three-phase electromagnets for generating a rotating magnetic field, whereby the electromagnets and the permanent magnet 7b cooperate with each other to thereby rotationally drive the second rotor 5b.

Accordingly, the second electromagnetic means 8b and magnets 7b form a drive for rotating the impeller. The drive therefore typically includes a second magnetic material provided in the impeller and at least one drive coil that in use generates a magnetic field that cooperates with the second magnetic material allowing the impeller to be rotated.

The first pump 2 includes a first pump chamber (or cavity portion) 2b and the first impeller 2a. The first impeller 2a can move axially while rotating with the first rotor 5a in the first pump chamber 2b. A first inlet port 2c is provided in a centre of an outer surface wall of the first pump chamber 2b, with an outlet port 2d being provided on a side wall of the first pump chamber 2b.

The second pump 3 includes a second pump chamber 3b and the second impeller 3a. The second impeller 3a can move axially while rotating with the second rotor 5b in the second pump chamber 3b. A second inlet port 3c is provided in a centre of an outer surface wall of the second pump chamber 3b, with an outlet port 3d being provided on a side wall of the second pump chamber 3b.

It will be appreciated that the pump chambers 2b, 3b may be provided with volutes to thereby assist with transfer of the fluid to the outlets 2d, 3d. The volutes maybe any combination of type spiral/single, split/double or circular/concentric, however the latter circular volute type is preferred if a journal bearing is used, as will be described in more detail below, as this configuration produces a stabilising radial hydraulic force for optimal journal bearing functionality.

Figure 3:
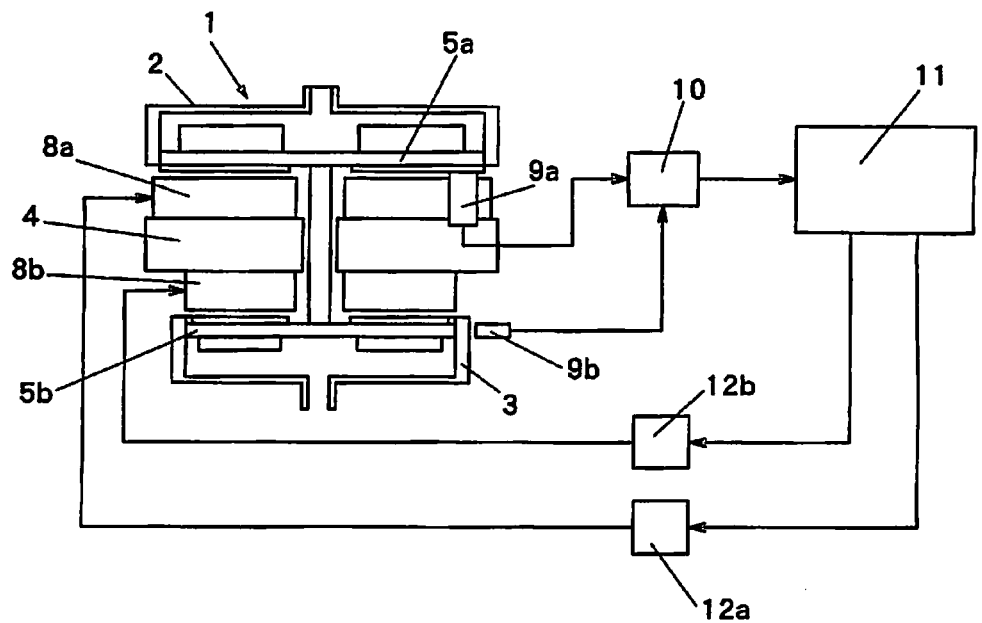
FIG. 3 is a block diagram of an example of a controller for the pump apparatus of FIG. 1.

FIG. 3 is a block diagram of a control system of the pump apparatus 1 of the present example.

In FIG. 3, reference numeral 9a denotes a first sensor that is provided corresponding to each electromagnet of the first electromagnetic means 8a of the first surface of the stator 4 and that is composed of eddy current sensors. The first sensor 9a detects an axial position of the first rotor 5a and inputs a detected signal into a controller 11 through an A/D converter 10. Additionally, inclination of the rotors is calculated in the controller 11 into which the detected signal is input from the first sensor 9a as will be explained hereinafter.

In this example, four first sensors 9a are provided corresponding to the four electromagnets 8a, with first detected signals of axial positions of the first rotor 5a and the second rotor 5b being obtained by calculating an average value of the detected signals from the four first sensors 9a in the controller 11. Additionally, second detected signals of inclination of the first and second rotors 5a and 5b are obtained from an average difference of the adjacent first sensors 9a, and from a distance between the first sensors 9a.

Note that an example using four first sensors 9a is explained above, but the inclination can be calculated in a case of the three or more first sensors 9a. Furthermore, in one example, particularly if a hydrodynamic bearing is used, inclination or tilt sensing may not be required.

Reference numeral 9b denotes a second sensor that is provided near the second rotor 5b and that detects rotational speeds of the first and second rotors 5a and 5b. The second sensor 9b inputs third detected signals of the rotational speeds into the controller 11 through the A/D converter 10.

The controller 11 implements a PID (Proportional-Integral-Derivative) control operation based on the first and second detected signals, outputs a control signal to the first electromagnetic means 8a through a drive circuit 12a, thereby controlling the axial position and the inclination of the first rotor 5a. Simultaneously, the controller carries out a PID control operation based on the third detected signals, outputs a control signal to the second electromagnetic means 8b through a drive circuit 12b, and controls the rotational speed of the second rotor 5b.

Next, usages and operations of the pump apparatus 1 of the present embodiment will be explained.

In one example, the pump apparatus 1 is used for a blood pump of an artificial heart. Namely, the first pump 2 operates so as to pump blood through the body as a left ventricle blood pump, and additionally, the second pump 3 operates so as to pump blood to the lungs as a right ventricle blood pump.

Rotational drive of the above-described pump is performed cooperatively by the permanent magnet 7b of the second surface of the second rotor 5b and the second electromagnetic means 8b of the second surface of the stator 4. The rotational speed of the first rotor 5a is the same as that of the second rotor 5b by virtue of the physical coupling between the rotors 5a, 5b, provided by the shaft 6.

In addition, during the rotation of the rotors 5, the first electromagnetic means 8a and the permanent magnet 7a cooperate with each other to thereby level the first rotor 5a and the second rotor 5b with an inclination control signal from the controller 11. Additionally, an attractive force between the first electromagnetic means 8a and the permanent magnet 7a is adjusted in accordance with a control signal of the axial position from the controller 11. This is performed in order to adjust a flow ratio of the first pump 2 to the second pump 3, by altering the axial position of the first rotor 5a and the second rotor 5b.

In particular, a force towards the second pump 3, generated as a sum of the attractive force between the first electromagnetic means 8a and the permanent magnet 7a, can be adjusted as described above. Accordingly this controls the levitation of the rotors 5a, 5b while adjusting the axial positions of the rotors 5a, 5b, and hence the impeller 5. This is balanced with an opposing force, towards the first pump 2 generated by an attractive force between the second electromagnet 8b and the permanent magnet 7b.

Thus, the drive is positioned adjacent the second cavity portion, and wherein the drive and second magnetic material are configured to result in an attractive force between the drive and the second rotor, whilst the magnetic bearing is positioned adjacent the first cavity, with the magnetic bearing and first magnetic material being configured to result in an attractive force between the magnetic bearing and the first rotor. In one example, the attractive forces are approximately balanced when the impeller is positioned at an approximately axially central position during normal circulatory conditions.

Figures 4, 5:
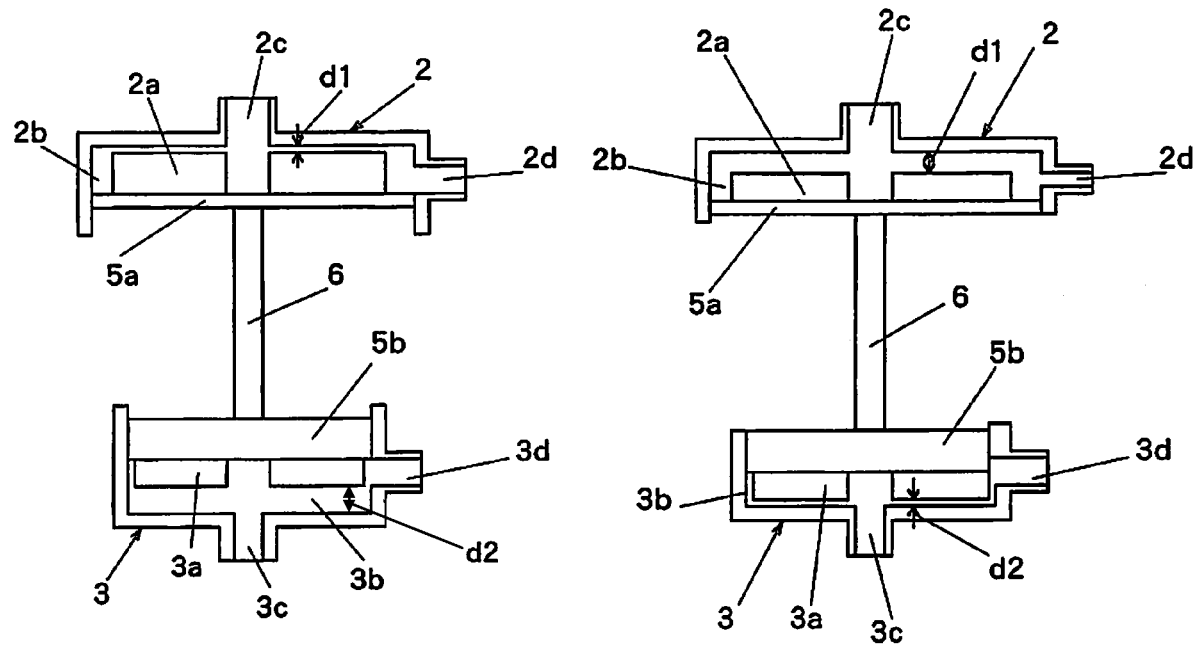
FIG. 4 is a sectional view of an example of a pump apparatus of FIG. 1 with the rotor in a first axial position.
FIG. 5 is a sectional view of an example of a pump apparatus of FIG. 1 with the rotor in a second axial position.

When the levitation of the rotors 5a, 5b is controlled and then the first rotor 5a moves upwardly, a gap $d_1$ between the first impeller 2a and a top surface wall of the first pump chamber 2b becomes smaller as shown in FIG. 4. At the same time, a gap $d_2$ between the second impeller 3a and a bottom surface wall of the second pump chamber 3b becomes larger. At this time, since the gap $d_1$ between the first impeller 2a and the top surface wall of the first pump chamber 2b is smaller in the first pump 2, backflow hardly occurs and an outlet flow from the outlet port 2d increases. Since the gap $d_2$ between the second impeller 3a and the bottom surface wall of the second pump chamber 3b is large in the second pump 3, even if discharge is performed by the second impeller 3a, backflow occurs in the gap $d_2$ and the outlet flow from the outlet port 3d becomes smaller.

In contrast, when the first rotor 5a moves downwardly, towards the stator 4, the gap $d_1$ between the first impeller 2a and the top surface wall of the first pump chamber 2b increases as shown in FIG. 5. The gap $d_2$ between the second impeller 3a and the bottom surface wall of the second pump chamber 2b also becomes smaller. At this time, since the gap $d_1$ between the first impeller 2a and the top surface wall of the first pump chamber 2b is larger in the first pump 2, even if discharge is performed by the first impeller 2a, backflow occurs in the gap $d_1$ and thereby an outlet flow from the outlet port 2d decreases. Since the gap $d_2$ between the second impeller 3a and the bottom surface wall of the second pump chamber 3b is smaller in the second pump 3, backflow hardly occurs and an outlet flow from the outlet port 3d increases.

Consequently, if a discharge amount of the left ventricle is increased, when the rotor is moved towards the first pump chamber 2b, the discharge amount of the left ventricle becomes large, and that of the right ventricle becomes small as described above.

Hence, the positions of the axial movement of the rotors 5 may be controlled by the control signals from the controller 11 so that a ratio of the discharge amount of the left ventricle to that of the right ventricle becomes a desired one.

Accordingly, in this example, the axial position of the impeller determines a separation between each set of vanes and a respective cavity surface, the separation being used to control the fluid flows from the inlets to the outlets. In one further example, the controller can therefore control the flows from the inlets to the outlets to alter the fluid flow to take into account different haemodynamic states. This can be achieved by determining movement of the impeller in a first axial direction, causing the magnetic bearing to move the impeller in a second axial direction opposite the first axial direction, determining an indicator indicative of the power used by the magnetic bearing and causing the magnetic bearing to control the axial position of the impeller in accordance with the indicator to thereby control a fluid flow between the inlets and the outlets. An example of such control will be described in more detail below.

Note that in the present example, an example is explained that the permanent magnet 7a is engaged with the bottom surface of the first rotor 5a, but the first rotor 5a may be formed of a magnetic material instead of engaging the permanent magnet 7a thereto.

In addition, in the present embodiment, an example is explained that the first rotor 5a and the second rotor 5b are connected to be fixed to the shaft 6 that passes through the centre through-hole of the stator 4, but they may be connected to be fixed with a plurality of rods located outside and near the side surface of the stator 4 and capable of vertical movement.

The pump apparatus 1 described above is a compact, simple structure, and is also controlled easily, so that the structure is the most suitable for a blood pump of an artificial heart. The apparatus can also be used for a blood pump of an artificial heart or for a pump that discharges a fluid by simultaneously adjusting a ratio of discharge amounts from the pump chambers 2b, 3b. Accordingly, in one example, a pump apparatus is provided that can easily control each discharge amount of a left ventricle blood pump and a right ventricle blood pump as a blood pump of an artificial heart.

The above described arrangement provides a number of advantageous effects. For example, the pump can provide a function of the left ventricle blood pump and a function of the right ventricle blood pump in one pump apparatus, which is compact and lightweight and thereby the equipment can be simplified, and which can be driven without any trouble over a long time by magnetic levitation means, and further in which discharge amounts of the right and left blood pumps can be easily controlled simultaneously.

In one example, a first rotor 5a above a stator 4 and a second rotor 5b thereunder are connected to each other with an axis of rotation 6a inserted into a centre through-hole 4a of the stator 4, and an acting force in an axial direction is generated by first electromagnetic means 8a of a first surface of the stator 4 with respect to a permanent magnet 7a of a second surface of the first rotor 5a, while second electromagnetic means 8b of a second surface of the stator 4 operates on a permanent magnet 7b of a first surface of the lower rotor 5b to rotationally drive the second rotor 5b, whereby a first portion of the pump apparatus operates as first pumping means 2 by first impeller vanes 2a on a first surface of the first rotor 5a, while a second portion of the pump apparatus operates as second pumping means 3 by second impeller vanes 3a of a second surface of the second rotor 5b.

Figure 6A:
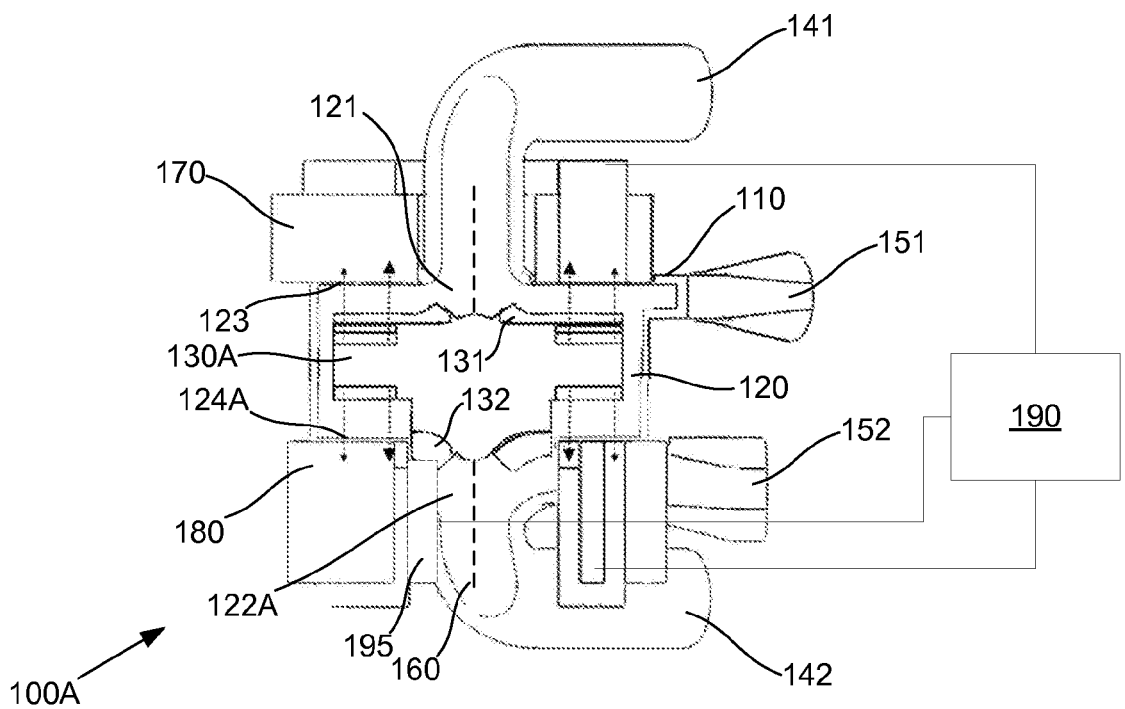
FIG. 6A shows a schematic cross sectional view of a second example of a heart pump.

A reference numerals list is set out below, with alternative terminology that can be used interchangeably with the terminology above being listed:

1—Heart Pump or Pump Apparatus
1a—First Part
1b—Second Part
2—First Pump or First Pumping Means
2a—First Impeller
2b—First Cavity Portion or First Pump Chamber
3—Second Pump
3a—Second Impeller
3b—Second Cavity Portion or Second Pump Chamber
4—Stator
4a—Connecting Tube or Center hole
5a—First rotor or Upper Rotor
5b—Second rotor or Lower Rotor
6—Shaft
6a—Axis of Rotation
7a—First Magnetic Material or First Permanent magnet
7b—Second Magnetic Material or Second Permanent magnet
8a—First Electromagnetic Means
8b—Second Electromagnetic Means
11—Controller or Control Section A second example of a heart pump will now be described with reference to FIG. 6A.

In this example, the heart pump 100A includes a housing 110 defining a cavity 120, containing an impeller 130A. The impeller 130A effectively divides the cavity 120 into first and second cavity portions 121, 122A. The housing 110 includes first and second inlets 141, 142 and corresponding first and second outlets 151, 152, which are in fluid communication with the first and second cavity portions 121, 122A, respectively.

The impeller 130A includes first and second sets of vanes 131, 132, such that rotation of the impeller 130A about a rotation axis 160 urges fluid from the inlets 141, 142 to the corresponding outlets 151, 152. In use, rotation of the impeller 130A is achieved using a drive, such as a magnetic drive 170. The magnetic drive 170 typically includes at least one coil positioned at a first end of the housing 110 adjacent the first cavity 121. In use, the coil generates a magnetic field that cooperates with magnetic material in the impeller 130A, allowing the impeller to be rotated. This tends to lead to an attractive force between the drive 170 and the impeller 130A that urges the impeller 130A in an axial direction towards the first cavity 121.

In use, a relative physical separation between the set of vanes 131, 132 and the corresponding cavity surfaces 123, 124A controls the relative efficiency of the vanes 131, 132 and hence the relative flows between the inlets 141, 142 and the corresponding outlets 151, 152. The position of the impeller 130A in an axial direction is typically controlled using a magnetic bearing 180. The magnetic bearing 180 typically includes at least one coil positioned at a second end of the housing 110 adjacent the second cavity 122A. In use, the coil generates a magnetic field that cooperates with magnetic material also in the magnetic bearing stator, which interacts with ferrous material within the impeller 130A, allowing the axial position of the impeller 130A to be controlled. This tends to lead to an attractive force between the magnetic bearing 180 and the impeller 130A, that urges the impeller 130A in an axial direction towards the second cavity 122A.

Although the drive 170 and bearing 180 are positioned adjacent the first and second cavity portions 121, 122A respectively, this is not essential and the positioning could be reversed, with the bearing 180 being positioned adjacent the first cavity portion 121 and the drive 170 positioned against the second cavity portion 122A. However, in general, as the drive needs to provide a rotational torque to the impeller 130A, this is easiest if the drive couples to the impeller 130A in the first cavity portion as the impeller 130A has a greater diameter at this point, which in turn maximises the torque of the drive 170.

The drive 170 and the bearing 180 are typically coupled to a controller 190, allowing operation of the heart pump 100 to be controlled. The controller is also typically coupled to a sensor, an example of which is described in more detail below, allowing the position of the impeller to be determined.

A third example of a heart pump will now be described with reference to FIG. 6B. In this example, similar reference numerals are used to designate similar features, and these will not therefore be described in any detail.

In this example, the heart pump 100B includes a modified second cavity 112B, having a surface 124B that extends across the housing 110, where the inlet is provided in the example of FIG. 6A. Accordingly, in this example, the heart pump 110 does include a second inlet or a second outlet. Furthermore, impeller 130B includes only a single set of vanes 131, positioned in the cavity 121, and includes an aperture 135 extending through the impeller 130B, for allowing blood to flow from the second cavity 122B to the first cavity 121, to thereby prevent stagnation between the impeller 130B and the second cavity surface 124B.

In use, the heart pumps 100A, 100B can be coupled to a subject to supplement the pumping action of one or both of the left and right ventricles of the heart.

For example, the heart pump 100A of FIG. 6A can be coupled to both the pulmonary and systemic circulatory systems, allowing the pump to operate as a BiVAD (Bi-Ventricular Assist Device), in which the pump supplements the pumping action of both the left and right ventricles of the heart. In this instance, the left ventricle and the right atrium are coupled to the first and second inlets 141, 142 respectively, whilst the first and second outlets 151, 152 and provide outflow to the aorta and the pulmonary artery, respectively.

In use, the heart pump 100A is arranged so that with the impeller 130A positioned at an approximately axially central point within the cavity 120, generally referred to as a nominal balance point, the pumping action provided by each set of vanes 131, 132 equates to the pumping action required by each of the left and right ventricles respectively. This can be achieved by selection of suitable dimensions, such as the length, height and shape of the respective vanes, and in general achieves a flow of approximately 5 L/min at each outlet 151, 152.

When the circulatory system is functioning correctly, the pressure within the first cavity portion 121 will be greater than the pressure in the second cavity portion 122A, approximately 100 mmHg as opposed to 20 mmHg. In this instance, blood flow between the first and second cavities 121, 122A is substantially prevented due to the presence of the impeller 130A. Depending on impeller geometry, this normal pressure differential may lead to a force on the impeller 130A, for example acting towards the second cavity portion 122A.

In one example, the heart pump is naturally balanced, so that any such forces on the impeller 130A including forces resulting from the pressure differential and the attractive forces arise caused by magnetic coupling between the impeller 130A and the drive 170, as well as between the impeller 130A and the bearing 180, are approximately equal when the impeller 130A is provided at a balance point.

As will be described in more detail below, the position of the balance point within the cavity 120 is controlled, and is typically positioned at an axial centre of the cavity 120 when the circulatory system is functioning correctly. This can be achieved by selection of suitable magnetic properties for the impeller 130A, the drive 170, as well as the bearing 180. In such a situation, the additional force that is required to be exerted by the magnetic bearing 180 to maintain the impeller 130A at the balance point is minimal, which is sometimes referred to as a "zero power configuration". In this regard, the term zero is understood to not necessarily be zero, but rather means that the power required is less than if such balancing were not present.

In this example, if there is a change in the relative pressures of the first and second cavity portions 121, 122A caused by an increase in pressure within the pulmonary circulatory system, and/or a decrease in pressure within the systemic circulatory system, then this will lead to a modified pressure differential. The modified pressure differential results in a net force on the impeller 130A, causing movement of the impeller 130A away from the balance point towards the first cavity portion 121, thereby reducing separation between the first set of vanes 131 and the first cavity surface 123. This increases the efficiency of the pumping effect in the systemic system, and decreases the pumping effect in the pulmonary system. This will reduce flow into the pulmonary circulatory system, whilst increasing the flow into the systemic circulatory system, which in turn will exacerbate the flow balancing problems in the pulmonary and/or systemic circulatory system.

Similarly, a decrease in pressure within the pulmonary circulatory system, and/or an increase in pressure within the systemic circulatory system, will also result in a net force causing movement of the impeller 130A towards the second cavity portion 122A. This reduces separation between the second set of vanes 132 and the second cavity surface 124A, thereby increasing the efficiency of the pumping effect in the pulmonary system, and decreasing the pumping effect in the systemic system, thus increasing the flow balancing problems in the pulmonary or systemic circulatory systems.

To address this situation, a control process is implemented, typically by the controller 190, which allows the position of the impeller 130A within the cavity 120 to be controlled, as will be described in more detail below.

It will be appreciated that the heart pump 1 described above with respect to FIGS. 1 to 5 can function in a similar manner, and this will not therefore be described in further detail.

However, it is also notable that differences exist between the heart pumps 1, 100A. In particular, in heart pump 1, the cavity portions 2, 3 are separated by a connecting tube 4a, whereas in FIG. 6A, the cavity portions 121, 122A are separated only by the impeller 130A. As a result, the minimum cross sectional area and the distance of the path along which fluid has to travel if it is to flow from one cavity portion to another is greatly increased in the heart pump 1 of FIGS. 1 to 5 than compared to the heart pump 100A. This helps reduce leakage between the heart pump cavity portions 2, 3, which can be desirable in some situations.

Leakage can additionally be controlled through appropriate selection of the relative diameters of the shaft 6 and the connecting tube 4a, which act to alter the minimal cross sectional area along the flow path, as well as through other factors, such as the presence of flow elements, such as ridges or troughs on the shaft or connecting tube surfaces.

In the example of FIGS. 1 to 5, the first and second electromagnetic means 8a, 8b act as a bearing and drive respectively. Accordingly, it will be appreciated that in this example, the drive 8b couples to the second rotor 5b, which has a diameter smaller than that of the first rotor 5a. Typically the diameters are 30-40 mm for the second rotor 5b, and 50-60 mm for the first rotor 5a.

In any event, coupling of the drive to a smaller part of the impeller 5 is the reverse of the preferred implementation of the heart pump 100A, in which the drive 170 couples to the larger diameter portion of the impeller 130A. In one example, this is as a result of a reduced differential diameter between the first and second rotors 5a, 5b, thereby reducing the torque benefit that could be obtained coupling the drive to the larger diameter portion of the impeller 5. However, it will be appreciated that any suitable arrangement could be used, so that the drive could couple to the larger rotor 5a.

Figure 6B:
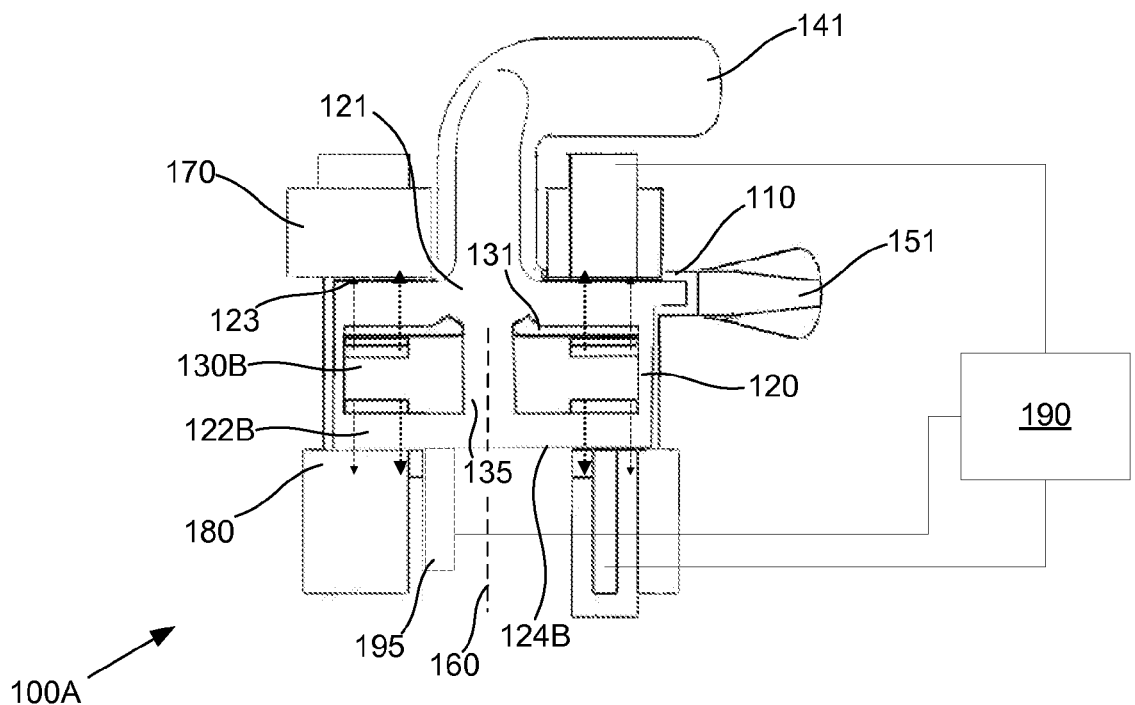
FIG. 6B shows a schematic cross sectional view of a third example of a heart pump.

In the example of the heart pump 100B of FIG. 6B this can be coupled to either the pulmonary or systemic circulatory systems, allowing the pump to operate as a VAD (Ventricular Assist Device), in which the pump supplements the pumping action of both either the left or right ventricles of the heart.

In this example, the heart pump 100B is arranged so that with the impeller 130B positioned at an approximately axially central point within the cavity 120, generally referred to as a nominal balance point, the pumping action equates to the pumping action required the respective ventricle. This can be achieved by selection of suitable dimensions, such as the length, height and shape of the respective vanes, and in general achieves a flow of approximately 5 L/min at the outlet.

In this example, the fluid pressure within the cavities 121, 122B will result in a pressure differential on the impeller 130B, depending on the configuration of the impeller 130B, as will be described in more detail below. The pump 100B is again naturally balanced, so that any forces on the impeller 130B, including forces resulting from the pressure differential and the attractive forces arise caused by magnetic coupling between the impeller 130B and the drive 170, as well as between the impeller 130B and the bearing 180, are approximately equal when the impeller 130B is provided at a balance point. Again, the balance point within the cavity 120 is typically positioned at an axial centre of the cavity 120 when the circulatory system is functioning correctly, so a "zero power configuration", is implemented.

In this example, if there is a change in the pressure within the cavities 121, 122B, this will result in a modified pressure differential on the impeller, causing movement of the impeller 130B away from the balance point. The direction in which this occurs depends on the pressure differential generated across the impeller 130B, which again could exacerbate flow problems.

Figure 7:
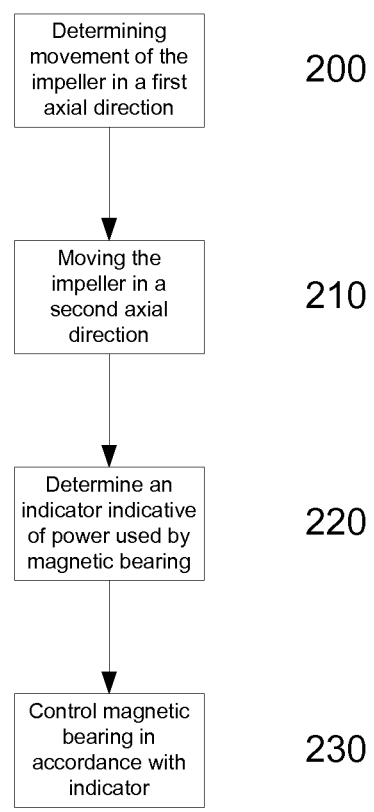
FIG. 7 is a flow chart of an example of a method of controlling a position of an impeller in a heart pump.

An example of a control process will now be described with reference to FIG. 7. This control process is equally applicable to the heart pump of FIGS. 1 to 5, as well as to the second and third example heart pumps 100A, 100B, of FIGS. 6A and 6B. Accordingly, the following description will focus generally on a heart pump 100, having a impeller 130, with the respective heart pump 100A, 100B being identified only when this has an impact on the process, and with the heart pump 1 being assumed to function in a manner substantially similar to that described with respect to the heart pump 100A.

In this example, at step 200, the process includes determining movement of the impeller 130 in a first axial direction in accordance with signals from a sensor 195. The sensor can be adapted to detect movement of the impeller 130 in any suitable manner. For example, this could be achieved through the use of pressure sensors capable of detecting changes in the relative pressures within the first and second cavity portions 121, 122, or within the systemic and pulmonary circulatory systems, which would in turn lead to movement of the impeller 130. Alternatively, this could be achieved by detecting a separation between the impeller 130 and a sensor 195, such as a suitable position sensor, as will be described in more detail below.

It will be appreciated that the first direction could be either towards the first or second cavity portions 121, 122, depending on the nature of the variation from the normal pressure differential, and in particular whether this is caused by an increase and/or decrease in either one or both of the systemic and pulmonary systems.

At step 210, the magnetic bearing 180 is used to move the impeller 130 in a second axial direction opposite the first axial direction. Thus, for example, this can involve increasing or decreasing the force applied by the magnetic bearing 180, thereby allowing the impeller 130 to be moved against the force caused by the change to the normal pressure differential between the two cavity portions 121, 122.

At step 220, an indicator indicative of the power used by the magnetic bearing 180 is determined. This may be achieved in any suitable manner, such as by monitoring the current drawn by the magnetic bearing 180. This could include, for example, monitoring the current used to maintain the impeller 130 at a constant axial position, or alternatively can involve monitoring the change in current drawn by the magnetic bearing 180 as the impeller 130 is moved in the second axial direction.

At step 230, the indicator is used to control the axial position of the impeller 130. This is typically performed so as to minimise the current drawn by the magnetic bearing 180, within any required constraints, thereby maintaining a zero power configuration, even in the presence of a change in the normal pressure differential. This situation results in a new balance position that is offset from the axial central position. In particular, in the above described configuration, as there are attractive forces between the impeller 130 and both the drive 170 and the magnetic bearing 180, the new balance position will be offset from the axial central position in the second direction.

Thus, if the impeller 130 is urged towards the second cavity 122, by an increase in pressure within the first cavity 121, then the new balance position will be located offset from the axially central position towards the first cavity 121. In this position, the attractive force between the drive 170 and the impeller 130 is increased, whilst the attractive force between the magnetic bearing 180 and the impeller 130 is decreased. This results in a greater net force towards the first cavity 121, balancing the increased force towards the second cavity 122 that is caused by the change in pressure differential.

In the example of the heart pump 100A, with the new balance position offset towards the first cavity 121, the reduced separation between the first set of vanes 131 and the first cavity surface 123 increases the pumping effect within the first cavity 121, thereby increasing the flow from the first outlet 151. Similarly there is a decrease in the pumping effect in the second cavity 122A, resulting in a reduction in flow from the second outlet 152. Accordingly, this operates to restore the normal flow balance of the circulatory system. It will be appreciated that once the normal pressure differential is restored, this will result in a net force towards the first cavity 121.

Applying the above described process will then return the impeller 130A to the normal balance position axially centred within the cavity 120.

Thus, for the heart pump 100A, the above described process operates to maintain zero power control by adjusting the position of the impeller 130A within the cavity 120 when a change in the normal pressure differential arises between the circulatory systems, allowing the impeller 130A to be provided at a new balance position. Furthermore, in one example, the inherent attractive forces between the impeller 130A and the drive 170 and magnetic bearing 180 result in a new balance position offset from the axial centre of the cavity 120, thereby controlling relative flows between the inlets 141, 142 and the corresponding outlets 151, 152, which in turn can be used to compensate for changes in vascular resistance in the circulatory systems.

It will therefore be appreciated that this control process allows the heart pump 100A to implement relative flow control whilst maintaining a zero power configuration.

In the example of the heart pump 100B, an increase in pressure within the cavities 121, 122B results in a pressure differential across the impeller 130B that moves the impeller 130B towards the first cavity 121. In this instance, the new balance position will therefore be offset towards the second cavity 122B, with the increase separation between the first set of vanes 131 and the first cavity surface 123 leading to a decrease in the pumping effect within the first cavity 121. This reduces the flow pressure, thereby counteracting the increased flow pressure within the first and second cavities 121, 122B.

Thus, for the heart pump 100B, the above described process operates to maintain zero power control by adjusting the position of the impeller 130B within the cavity 120 when a change in the normal pressure differential across the impeller arises due to a change in pressure within the respective circulatory system to which the pump 100B is attached. Unlike the BiVAD application for the pump 100A, correcting for the pressure differential is more important than correcting relative flows between the circulatory systems, as relative flow will be influenced by the ventricle not attached to the pump 100B. Thus, in the VAD example for the pump 100B, the inherent attractive forces between the impeller 130B and the drive 170 and magnetic bearing 180 result in a new balance position offset from the axial centre of the cavity 120, thereby counteracting any pressure changes, which in turn can be used to compensate for changes in vascular pressure in the circulatory systems.

It will therefore be appreciated that this control process allows the heart pump 100B to implement pressure control whilst maintaining a zero power configuration. In this example, if flow control is required, this can be achieved by adjusting the rotation speed of the impeller 130B. It will be appreciated that this is less complex than attempting to alter the rotation rate of the impeller 130A in the heart pump 100A, which could result in an undesirable flow differential arising due the different configuration of the first and second sets of vanes 131, 132.

Whilst the above described process may be achieved in any suitable manner, in one example, this is achieved by the controller 190. Accordingly, the controller 190 is typically adapted to control the drive 170 to cause rotation of the impeller 130. In addition to this, the controller 190 will monitor the power drawn by the magnetic bearing 180, and use this to control the magnetic bearing 180, and hence the axial position of the impeller 130, as will be described in more detail below.

Figure 8:
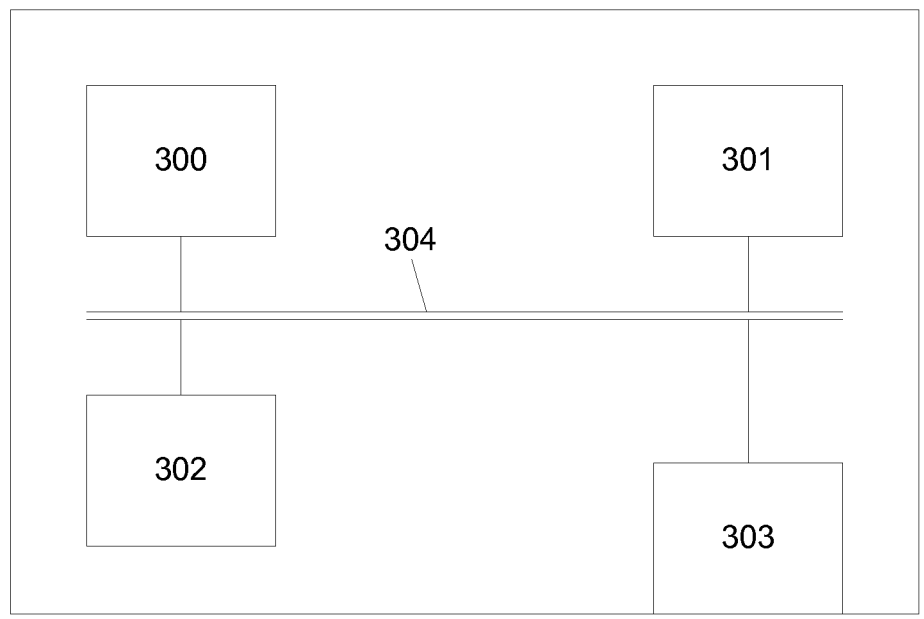
FIG. 8 is a schematic diagram of an example of a controller.

It will be appreciated from this that any suitable form of controller may be used, and an example controller will now be described in more detail with respect to FIG. 8.

In this example the controller 190 includes a processor 300, a memory 301, an optional input/output device (I/O device) 302, such as input buttons, a key pad, display or the like, or an optional external interface 303, allowing the controller 190 to receive signals from the sensor 195, and provide control signals to the drive 170 and the magnetic bearing 180. It will therefore be appreciated that the controller 190 may be in the form of a suitably programmed processing system, such as a computer, laptop, palm top, PDA, or alternatively may be specialised hardware, a programmable logic controller, field programmable gate array (FPGA) or the like.

In one example, the controller 190 is formed from custom micro-electronics, allowing the controller 190 to be physically implanted together with the heart pump, in a subject. Alternatively, the controller 190 could be used to control the heart pump 100 via wireless connections, or the like.

In use, the processor 300 executes instructions, typically stored in the memory 301, allowing the processor 300 to perform the control processes described herein. In particular, the processor 300 receives signals from the sensors 195 to allow an impeller position to be determined. The processor 300 then determines if modification of the operation of the bearing 180, and/or the drive 170 is required, and if so generates appropriate signals that are applied to the bearing and/or drive as required.

It will be appreciated that the controller 190 could also be implemented in the heart pump 1 of FIGS. 1 to 5 by replacing the controller 11.

An example of a process for using the controller 190 to control the position of a heart pump impeller will now be described with reference to FIG. 9. For the purpose of example, this will be described with respect to the heart pump 100A of FIG. 6A, although it will be appreciated that similar operation will occur for the heart pumps 1 and 100B.

In this example, at step 400, the controller 190 monitors axial position of the impeller 130A using the sensor 195, and determines if the impeller has moved at step 410, as a result of a change in pressure differential between the pulmonary and systemic circulatory systems. This typically involves monitoring signals from the sensor 195 to determine if a separation between the impeller 130A and the sensor 195 has altered, thereby signifying that the impeller 130A has moved from a current balance position. The current balance position may correspond to the normal balance position if the circulatory systems were previously functioning in accordance with normal haemodynamics, although this is not essential.

At step 420, the controller determines a direction of the axial movement, by determining for example if the separation between the sensor 195 and the impeller has increased or decreased, and uses this to cause the magnetic bearing to cause opposing movement of the impeller 130A, at step 430, thereby moving the impeller back 130A towards the balance position.

At step 440, the controller determines the indicator based on rate of change of current used by magnetic bearing 180 as the impeller 130A is moved back towards the balance position. The indicator is compared to a predetermined value at step 450, to determine if the indicator, and hence the power consumption by the magnetic bearing 180 is acceptable at step 460. The value will therefore typically represent a minimal power usage by the magnetic bearing 180 that satisfies zero power requirements, and this is typically previously determined and stored in the memory 301 of the controller 190, prior to initial operation of the heart pump 100.

It will be appreciated that in general the power consumed by the magnetic bearing 180 decreases as the impeller 130A nears a new balance position associated with the changed pressure differential between the circulatory systems, and accordingly, this can be used to indicate if the impeller 130A has reached a new balance position.

If it is determined that the indicator is not successful at step 460, then the process moves on to step 470 to determine the axial position of the impeller 130A. The axial position is then compared to position limits at step 480 to determine if the impeller 130A is within operational positional limits at step 490. This is performed to ensure that the impeller 130A does not become too close to the first or second cavity surfaces 123, 124A, which could impact on the impeller performance. Again, the positional limits are typically previously determined values stored in the memory 301.

In the event that the impeller 130A is still within positional limits but has not yet reached the new balance point, then the process returns to step 430, to continue causing movement of the impeller 130A.

Otherwise, in the event that it is determined either that the new balance point has been reached, at step 460, or if positional limits have been reached at step 490, then movement of the impeller 130A is halted at the current position, which therefore represents an axial position as close to the balance point in a zero power configuration as is achievable.

The process can then return to step 400 allowing the process to be repeated in the event that further relative pressure changes occur between the systemic and pulmonary systems.

As described above, the configuration is such that the new balance point will counteract any variation away from a normal balance of left/right flow, thereby returning the circulatory systems to the normal flow balance required by normal haemodynamics.

If applied to the heart pump 100B, the above described process counteracts any pressure changes within the circulatory systems, returning the system to the normal haemodynamic pressure.

An example of the drive 170 and the magnetic bearing 180 for the heart pumps 100A, 100B is shown in FIGS. 10A to 10F.

In this example, the magnetic bearing 180 includes three evenly spaced 120° U-shaped bearing stator cores 181. Turns of copper wire 182 are wound about a radially outer foot of each stator core 181 to produce flux directed towards an iron core 185 attached to the impeller 130 (not shown in this example). A custom NdFeB permanent magnet 183 may be attached to the radially inner foot of each core to provide bias flux to the magnetic flux path. This permanent magnet may also be located on a impeller 130, or in the section bridging the inner and outer pole feet 184, and should preferably be of high magnetic strength (grade N52). The axial bearing magnetically couples to the iron core 185, which is made of a ferromagnetic material, and is mounted in the impeller 130.

The drive 170 typically includes a slotted axial flux motor core constructed with up with 12 poles, but is preferably constructed from a stator 171 having six poles 173 on which concentrated copper coils 172 are wound. The motor stator 171 is electromagnetically coupled to circumferentially spaced permanent magnets 174 having opposing polarities that alternate between North 174a and South 174b Poles, and are attached to a ferromagnetic core 175, mounted in the impeller 130.

Each of the bearing stator 181, motor stator 171 and ferromagnetic cores 175, 185 are preferably composed of material that exhibits high electrical resistivity and high magnetic permeability, such as an iron-cobolt or iron-silicon alloy. A suggested material is VACOFLUX 48 (Vacuumschmelze GMBH & CO. KG, Germany). The material may be laminated to reduce eddy current losses.

Axial attractive force $f_z$, and the motor torque $\tau_z$ produced by the magnetic drive and bearing systems 170, 180 are derived from Eq. (1) and Eq. (2). The parameters used in each equation are listed in TABLE 1.

TABLE 1

| | Parameters of the equations |
|---|---|
| $B_R$ | The peak flux density of the motor |
| $B_S$ | The peak flux density of the stator |
| M | The pole pair number of the motor |
| $\omega$ | The rotating speed of the impeller |
| $\phi$ | The phase difference |
| $r_1$ | The inner radius of the impeller |
| $r_2$ | The outer radius of the impeller |
| z | The equivalent distance of the air gap |
| $\mu_0$ | The permeability of vacuum |

$$f_z = \frac{(r_2^2 - r_1^2)\pi}{4\mu_0}[B_R^2 + 2B_R B_S \cos\phi + B_S^2] \quad (1)$$

$$\tau_z = \frac{zM(r_2^2 - r_1^2)\pi}{2\mu_0} B_R B_S \sin M\phi \quad (2)$$

The stator ($B_s$) and the permanent magnet flux of the impeller ($B_r$) are assumed to follow a cosine waveform magnetic flux density and as described by Eq. (3) and Eq. (4)

$$B_S(\theta,t) = B_S \cos(\omega t - M\theta) \quad (3)$$

$$B_r(\theta,t) = B_R \cos(\omega t - M\theta - \phi) \quad (4)$$

The number of turns in the coils 172, 182 and the geometric parameters of the permanent magnets 174, 183 produce this flux.

Figure 11A:
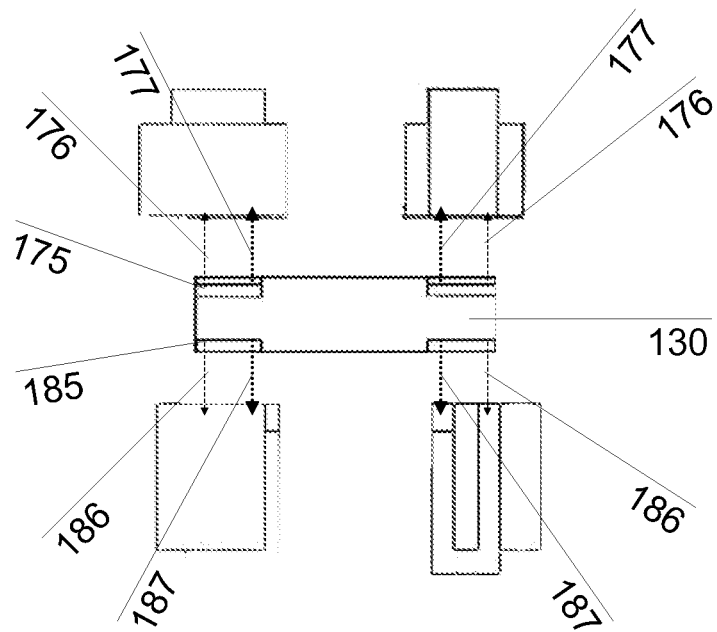
FIG. 11A is a schematic side illustrating the operation principle of axial position control by the magnetic bearing.

The operation principle of axial position control by the magnetic bearing is shown in FIG. 11A. Changing the magnitude of the motor stator and the magnetic bearing electromagnetic flux $B_S$ 176, 186 can control the axial displacement of the impeller 130. The motor torque is also controlled changing the phase difference $\phi$.

The permanent magnets 174, 183 in the drive 170 and the bearing 180, each produce a static bias flux 177, 187 in order to reduce the power requirements of the system. The attractive force produced by these magnets 174, 183 is in balance when the impeller 130 is located in the middle of the cavity 120. Therefore, the control flux 176, 186 produced by the coils 172, 182 in the drive 170 and the bearing 180, respectively, is required only to stabilise the impeller's axial position and overcome disturbance forces.

The control flux 186 generated by the bearing 180 can increase or decrease the effective attraction between the impeller 130 and the bearing 180 by generating a field that is complementary to or counter to the magnetic field generated by the permanent magnet 183. This controls the net magnetic field between the bearing and the bearing magnetic material, which in turn allows the position of the impeller 130 to be controlled in either direction within the cavity 120.

Feedback control of the impeller's axial position is achieved in response to impeller displacement, which may be detected by three positional sensors 195A, 195B, 195C, such as eddy current sensors (U5B, Lion Precision, Minn., USA). These displacement measurements are feedback parameters used by a control algorithm to stabilize the system. Control gains are output to a power amplifier, which generates the required current in the corresponding coil to alter the flux density in the magnetic gap and thus attractive force to maintain impeller levitation. Similarly, the motor controller generates the three phase current for the motor coils to provide synchronous rotation. This rotation may use feedback parameters of rotational speed derived from hall effect sensors or back EMF recordings to control rotational speed.

Figure 11B:
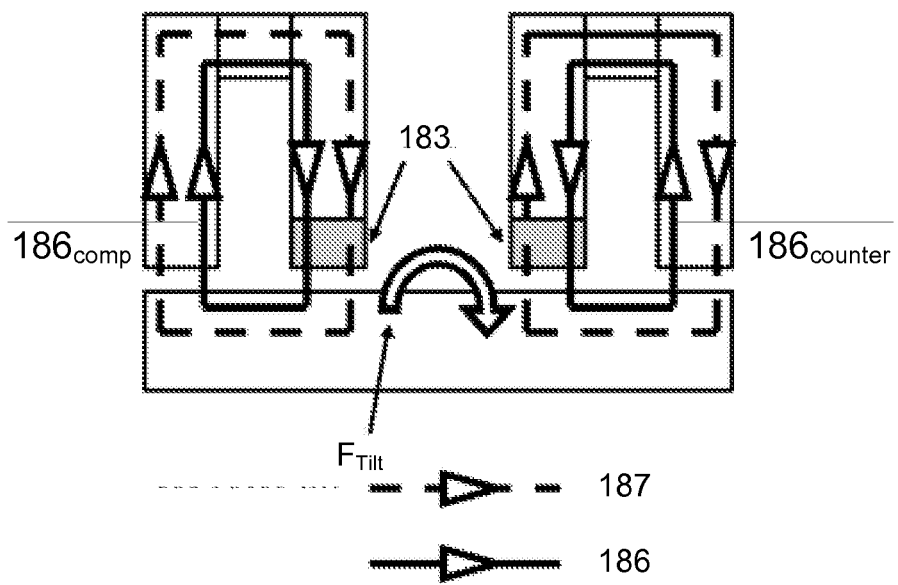
FIG. 11B is a schematic side illustrating the operation principle of tilt control by the magnetic bearing.

The operation principle of tilt control by the magnetic bearing is shown in FIG. 11B. The constant bias flux 177, 187 is produced by the permanent magnets 174, 183. When the impeller tilts, the electromagnetic control flux 176, 186 produced by the axial bearing 180 in the side that the impeller 130 approaches is decreased, by applying a counter flux $186_{counter}$, while the flux in the other side is increased, by applying a complementary flux $186_{comp}$, thereby generating a restoring tilt force $F_{Tilt}$.

It will be appreciated that similar drive and bearing arrangements can be implemented in the heart pump 1 of FIGS. 1 to 5, albeit with these being arranged between the cavity portions 2, 3, as previously described.

The manner in which the impeller position is maintained will now be described with reference to FIGS. 12A to 12C. This will be described with reference to second and third example heart pumps 100A, 100B, of FIGS. 6A and 6B. Accordingly, the following description will focus generally on a heart pump 100, having a impeller 130, with the respective heart pump 100A, 100B being identified only when this has an impact on the process. It will also be assumed that the heart pump 1 functions in a manner substantially similar to that described with respect to the heart pump 100A, with the impeller 5 acting as the impeller 130, and this will not therefore be described in further detail.

The controller 190 attempts to maintain a stable axial position of the impeller 130 in the centre of the pump cavity 120, as shown in FIG. 12A. In this regard, with the impeller centrally positioned, the static bias flux 177A, 187A produced by these magnets 174, 183 is in balance and consequently only minimal control flux 176A, 186A is required to be produced by the drive 170 and bearing respectively.

The introduction of a static disturbance force F, shown in FIG. 12B, attempts to displace the impeller 130 from this central position, in this case towards the cavity portion 121. A slight deviation of the axial position of the impeller 130 engages the 'zero position' controller 190, which increases the magnetic control flux 186B generated by the bearing 180, in order to counteract these forces F and maintain the notional centralised 'zero' position resulting in an increase in magnetic power used by the magnetic bearing 180.

However, by implementing a 'zero power' controller 190, the notional centralised axial position of the impeller 130 is not fixed to a physically central position within the cavity 130, and will change in response to the external disturbance forces.

In the above example, the application of a disturbance F toward the cavity portion 121 will cause the controller 190 to move the impeller 130 in the opposite direction, toward the bearing 180, until this disturbance force is counteracted by the increase in permanent magnetic attraction of the bearing bias flux 187C and subsequent reduction of motor bias flux 177C. This allows the electromagnetic control flux 186B to be reduced until the motor and bearing control flux 176C, 186C are minimal and are once again used only to stabilise the impeller in the new axial position.

As briefly mentioned above, controlling the magnetic bearing in zero power mode may be advantageous when operating the heart pump in the cardiovascular system, which is constantly adapting and changing its physiological parameters. These parameters particularly affect the pressure development within the heart pump, which impose a static disturbance hydraulic force on the impeller in the axial and radial directions.

The ability to alter the hydraulic output of a VAD or BiVAD is important to enable effective physiological operation within the cardiovascular environment. Changes in perfusion requirements due to alterations in a persons physical state must be met by the heart pump. Furthermore, the possibility of heart chamber collapse due to over-pumping of the heart pump must be prevented, or rectified shortly after such an event occurs, by reducing the heart pump outflow.

The most common technique to achieve this alteration of hydraulic performance is a change in impeller rotational speed. However, axial displacement of the impeller within the pump cavity also changes the hydraulic output of the pump, by inducing changes in flow leakage from the high pressure outlet to low pressure inlet. This technique effectively alters the energetic efficiency of the impeller vane set, and is most effective when a semi-open (i.e. without top shroud) impeller is used.

Figure 13C:
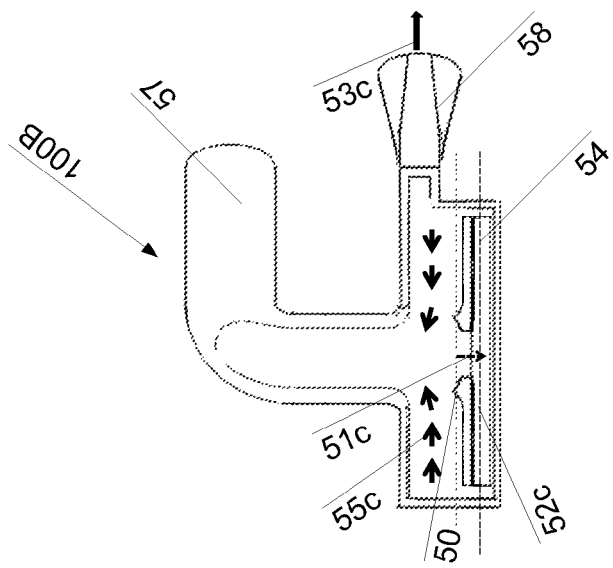
FIGS. 13A to 13C are schematic side views illustrating the manner in which a single sided impeller position is relocated to influence device outflow.
Figure 13B:
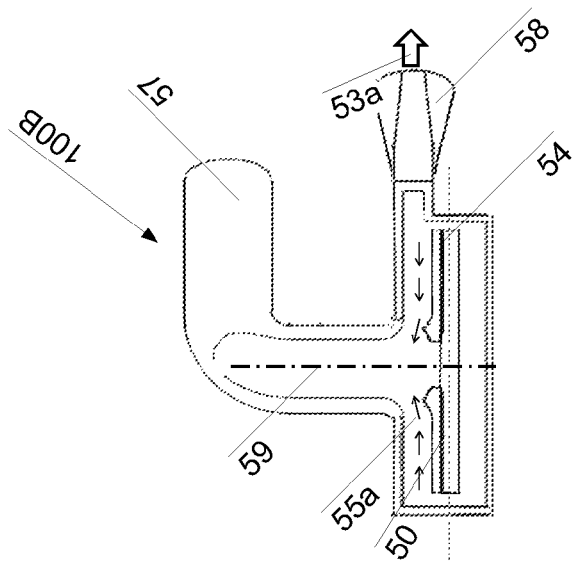
Figure 13A:
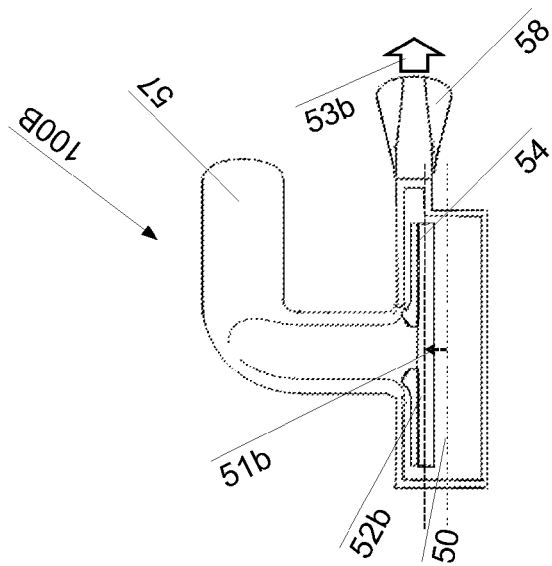

With reference to a single VAD, such as the heart pump 100B depicted in FIGS. 13A to 13C, centrally locating an impeller 54 within the pump cavity 50 and operating at a set rotational speed about an axis 59, the desired haemodynamics are produced for the circulatory system in need of support, as shown in FIG. 13B. Without changing the speed, shifting the impeller along its rotational axis 59 away from inlet 57 as shown by the arrow 51c effectively increases the clearance above the impeller vanes. This motion reduces the VAD outflow at the outlet 58 as shown by the arrow 53c, in FIG. 13C. The reduction of outflow is a direct result of an increase in leakage from the high pressure outlet 58 to low pressure inlet 57, as shown by the arrows 55c. Similarly, shifting the impeller toward the inlet 57, as shown by the arrow 51b has the opposite effect, i.e. VAD outflow increases, as shown by the arrow 53b, in FIG. 13A.

The axial motion of the impeller 130B can therefore be used to deliver sufficiently variable output flow from the VAD to meet the physiological requirements of the cardiovascular system at a set rotational speed. This effect is more pronounced when the impeller blade height is low and the ratio of impeller blade height to axial clearance is approx 3:1 (blade height=1.4 mm, starting axial clearance gap=0.5 mm), and sufficient outflow variation achieved with a movement of +/−0.3 mm.

In a specific application, the ability to acutely alter the left and right outflow of a BiVAD system is important, especially in the post operative period, to accommodate relative changes in systemic and pulmonary vascular resistance, the relative level of ventricular contractility, alleviation of acute pulmonic or systemic congestion, and to prevent suckdown by maintaining adequate atrial filling pressures. This requirement is again achieved by axially displacing the impeller 130A within a dual chambered heart pump, such as the heart pump 100A, thereby maintaining a long term balance of left and right flows.

Figure 14C:
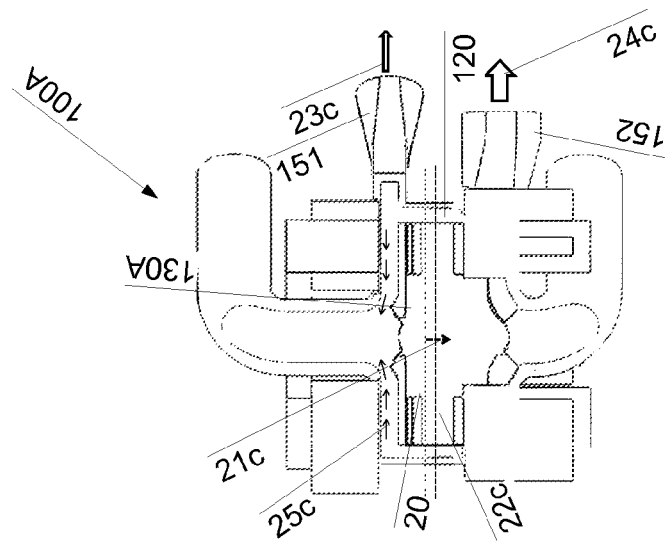
FIGS. 14A to 14C are schematic side views illustrating the manner in which a dual sided impeller position is relocated to influence device outflow.
Figure 14B:
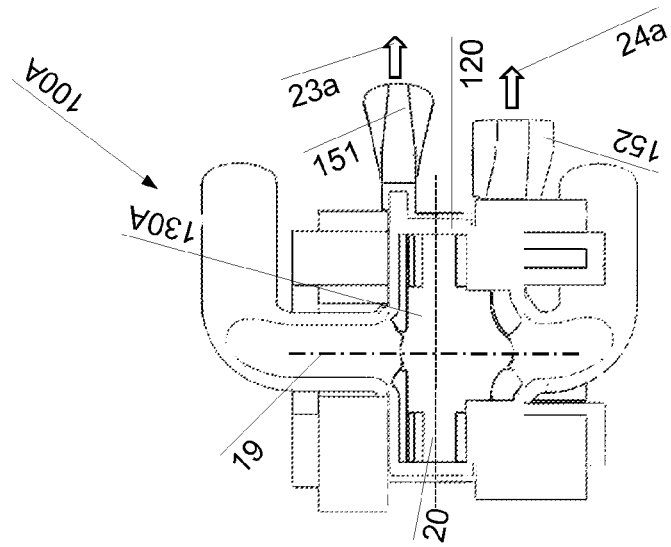
Figure 14A:
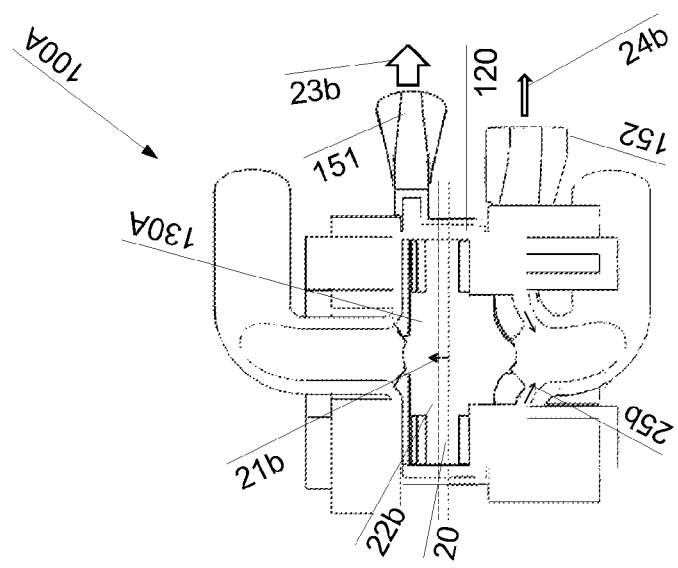

With reference to FIGS. 14A to 14C, an example of the effect of axial position on relative flows for a BiVAD, such as the heart pumps 1, 100A will now be described. This example is described with respect to the heart pump of FIG. 6A, and accordingly, similar reference numerals are used to designate similar features, although it will be appreciated that the techniques are equally applicable to the heart pump 1 of FIGS. 1 to 5.

In this example, with the impeller 130A located within the pump cavity 120, at the physical axial centre of the cavity, as shown by the line 20, and operating at a set rotational speed of approximately 2300 rpm about an axis 19, this results in the desired haemodynamics of 100 mmHg (LVAD) and 20 mmHg (RVAD) being produced for the systemic and pulmonary systems. Accordingly, the flows via the first and second outlets 151, 152 are in balance at approximately 5 L/min, as shown by the arrows 23a, 24a in FIG. 14B. The exact rate of flow from the left cavity is slightly higher than the right cavity, due to the natural outflow differential of the heart caused by the bronchial circulation.

Without changing the speed, shifting the impeller 0.3 mm along its rotational axis 19 toward the second cavity portion 122A, as shown by the arrow 21c reduces the axial clearance above the RVAD vanes (to 0.2 mm), while simultaneously increasing the clearance above the LVAD vanes (0.8 mm). This motion improves the RVAD outflow via the outlet 152, as shown by the arrow 24c while reducing the LVAD outflow via the outlet 151, as shown by the arrow 23c, in FIG. 14C. The reduction of outflow is a direct result of an increase in leakage from the high pressure outlet 151 to low pressure inlet 141, as shown by the arrows 25c.

Similarly, shifting the impeller from the central position toward the first cavity 121, as shown by the arrow 21b has the opposite effect. For example, while maintaining arterial pressures, this 0.3 mm movement toward the LVAD cavity 121 increases left outflow to 6.4 L/min, as shown by the arrow 23b while right outflow reduces to 4.6 L/min, as shown by the arrow 24b, in FIG. 14A, representing an instantaneous flow differential of 1.8 L/min (36%). This axial motion can therefore be used to accommodate the required variable flow output from left and right hearts at a set rotational speed. This effect is more pronounced when the impeller blade height is low and the ratio of impeller blade height to axial clearance is approx 3:1.

Figure 15:
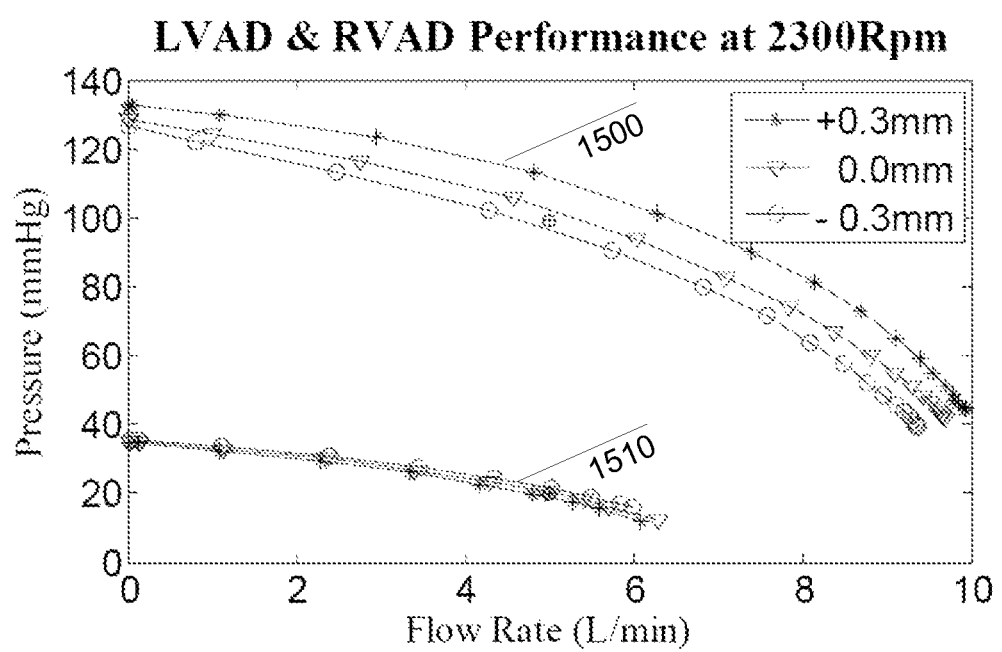
FIG. 15 is a graph illustrating the relative hydraulic performance of the left and right flows in an example BiVAD.
Figure 16A:
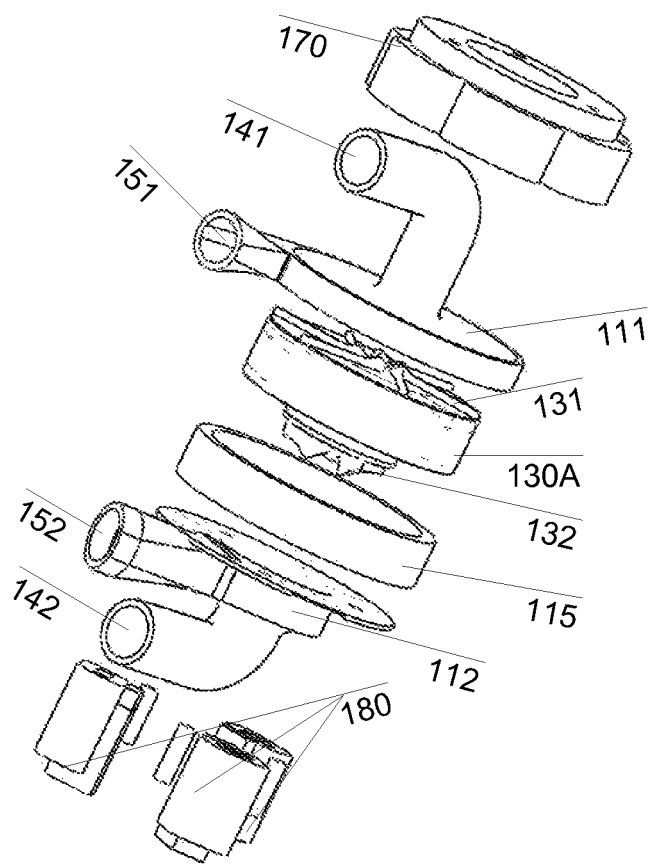
Figure 16B:
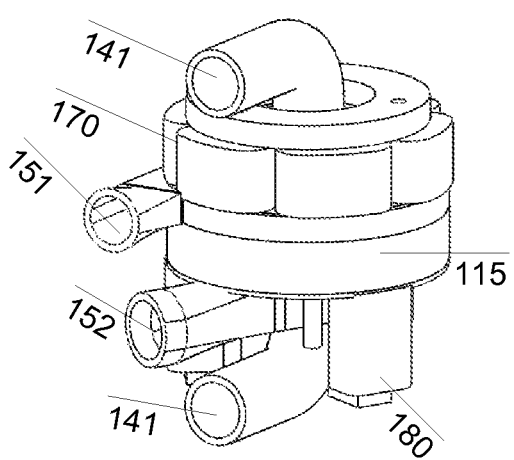
Figure 16C:
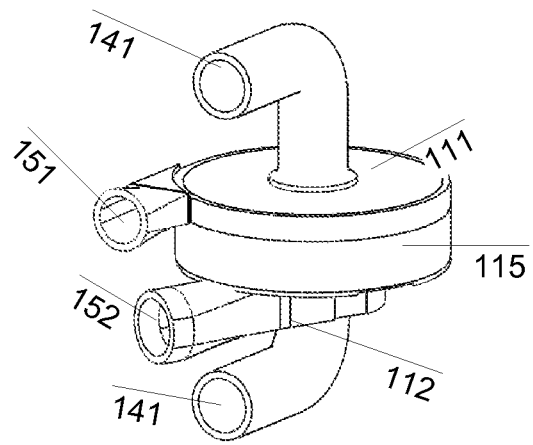
Figure 16G:
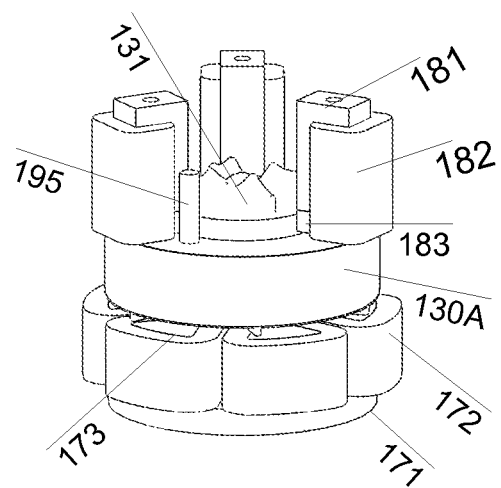
Figure 16H:
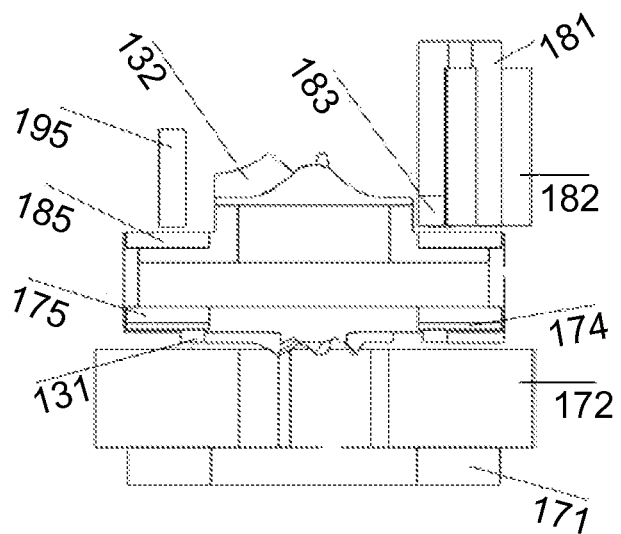

A graph showing examples of the relative performances of the pump, and in particular the pressure and flow at the outlets 151, 152, is shown at 1500, and 1510 respectively, in FIG. 15.

An example BiVAD configuration heart pump similar to the heart pump 100A of FIG. 6A, will now be described, with additional features being shown in FIGS. 16A to 16H. It will be appreciated that similar features may also be implemented in VADs, where appropriate.

In this example, the heart pump draws inflow from the right atrium via the second inlet 142 and from the left ventricle via the first inlet 141, and provides outflow to the pulmonary artery via the second outlet 152 and to the aorta via the first outlet 141. In this example, the first and second sets of vanes 131, 132 are mounted on a shared rotating hub to form a magnetically and hydro-dynamically suspended centrifugal impeller 130A. The first and second sets of vanes 131, 132 have a different outer diameter to produce the pressure required of the systemic and pulmonary systems at a common rotational speed, as described above. The differential in flow required from the left and right hearts is achieved by alteration of axial clearance above each semi-open VAD impeller.

The suspension system incorporates a hydrodynamic journal bearing 115, whilst volutes 111, 112 are provided as part of the housing 110, to thereby assist with transfer of the fluid to the outlets 151, 152. The volutes may be any combination of type spiral/single, split/double or circular/concentric, however the latter circular volute type is preferred, as this configuration produces a stabilising radial hydraulic force for optimal journal bearing functionality.

It will be appreciated that in the heart pump 1 of FIGS. 1 to 5 a hydrodynamic bearing could be implemented as part of the shaft 6. In one example, to achieve this, a separation between the shaft 6 and the connecting tube 4 is configured to be between 0.05 mm and 0.1 mm.

As outlined above, axial hydraulic force is imposed on the impeller 130A due to the build up of pressure within the left and right cavities. A differential of these pressures acting on the top and bottom impeller faces will produce a resultant force in either the positive or negative axial direction.

For the condition of dual heat support, the most important parameter to maintain is the balance of left and right flows from each supporting pump. Mismatch of flows may lead to the potentially disastrous situation of left or right heart chamber collapse. Application of the zero power controller, and its ability to favourably adapt device performance is described below for a number of foreseeable physiological conditions to be encountered by the BiVAD.

FIGS. 17A to 17D shows the resultant axial force development on a double sided impeller 130A during a variety of common conditions. Whilst this is described with respect to the impeller 130A, the techniques are equally applicable to the impeller 5 of FIGS. 1 to 5.

During diastole, the force acting on the face of the semi open LVAD impeller decreases from the outer diameter to the inner diameter, in proportion to the pressure development along this path. This is balanced by the force acting beneath the impeller 130A, which is composed of the section exposed to the high LVAD outlet pressure (which does not reduce as much with reducing diameter), and the RVAD impeller section exposed to the lower pressure developed in the RVAD cavity.

Figure 17A:
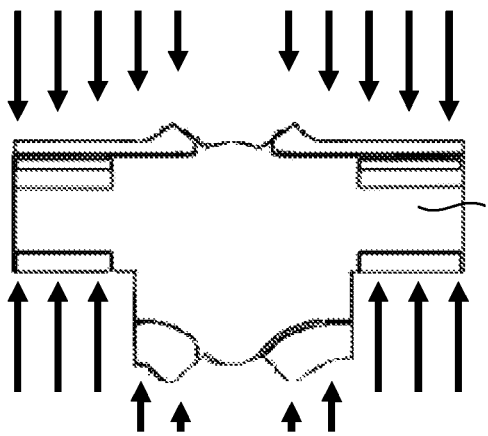
FIGS. 17A to 17D are schematic diagrams illustrating the resultant axial force development on the impeller of a BiVAD during a variety of common conditions.
Figure 17B:
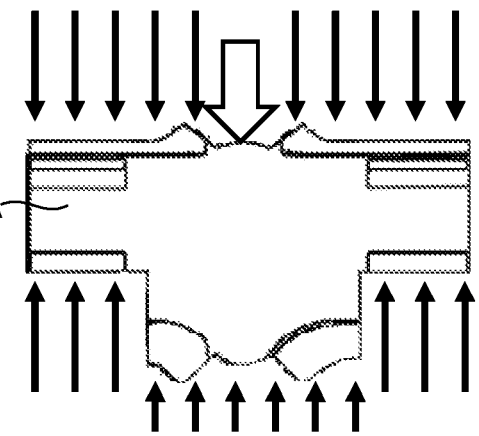

This balance is destroyed during systole, as shown in FIG. 17B. In this example, the left ventricular pressure acts across the entire LVAD impeller face, which cannot be matched by the lower RVAD pressure. Due to the impulse nature of this disturbance and damping of the blood, the actual force to be countered by the magnetic bearing is lower than the static differential would suggest.

Figure 17C:
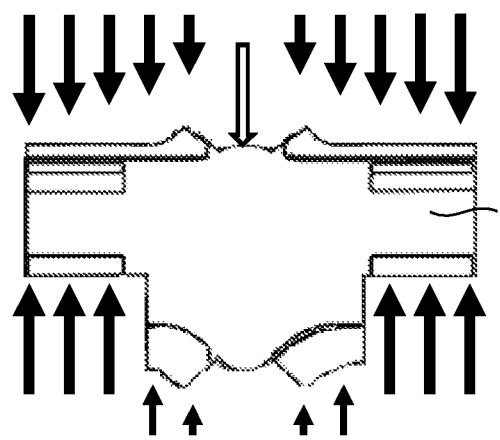

The effect of an increase in systemic vascular resistance (SVR) on pressure development and thus force generation is described in FIGS. 17A, 17B and 17C. Increasing SVR acts to increase the pressure within the LVAD first cavity 121, which in turn produces a force toward the RVAD second cavity 122A. The same resultant force is produced for a decrease in pulmonary vascular resistance (PVR). Using this logic, an opposite force is produced toward the LVAD cavity when SVR is decreased and/or PVR is increased.

Figure 17D:
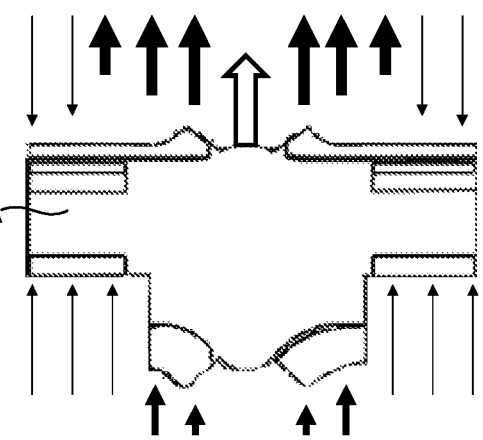

Finally, the force generated on the impeller during instances of left heart chamber collapse is described in FIG. 17D. In this instance, the pressure generated in the inlet cannula drops well below 0 mmHg, and the outlet correspondingly drops to a low value of pressure. This combination contributes to a large axial force toward the LVAD cavity.

FIGS. 18A to 18C describe the adaptation of the heart pump 100A to alterations in relative vascular resistance. The example presented is for a relative increase in SVR compared to PVR, but could also depict a relative decrease in PVR compared to SVR. The exact opposite would occur with a relative decrease in SVR or increase in PVR. Furthermore, whilst this is described with respect to the heart pump 100A, the techniques are equally applicable to the heart pump 1 of FIGS. 1 to 5.

During normal operation shown in FIG. 18A, the impeller 130A is positioned centrally within the cavity 120, and the left and right outflows from the first and second inlets 151, 152 are in balance, as shown by the arrows 36a, 35a. As the impeller 130A is located in the centre of the pump cavity 120, the bearing and motor PM bias forces, shown by the arrows 34a, 31a, are also in balance. Electromagnetic control flux forces from the drive 170 and the bearing 180 are minimal, as shown by the arrows 32a, 33a, being required only for stabilisation and to account for dynamic disturbances.

However, an increase in SVR, as shown in FIG. 18B, causes a decrease in LVAD flow from the outlet 151, as shown by the arrow 36b, and an increase in LVAD cavity pressure, which, as described earlier in FIG. 17C, results in a static axial hydraulic force vector toward the RVAD cavity 122A. To maintain the impeller 130A in the central position, the magnetic bearing flux must increase in magnitude (and thus power) to generate a counter field opposing that of the permanent magnets 183, as shown by the arrow 33b, to provide a restoring force.

However, this elevated SVR must be overcome to restore LVAD outflow. Implementing the 'Zero power' controller as described above, will cause the impeller to move toward the LVAD cavity 121 until the disturbance force shown by arrow 30 is balanced by the increase in permanent magnet bias flux from the drive 170, as shown by the arrow 31c. In this equalised position, electromagnetic control flux is once again minimal, and required only for dynamic disturbance forces, thus power consumption is reduced. Most importantly however, LVAD flow from the outlet 151 increases, as shown by the arrow 36c, whilst RVAD flow from the outlet 152, as shown by the arrow 35c slightly decreases, and the balance is maintained. Rotational speed may also be increased to simultaneously increase both LVAD and RVAD flow, should this be required to maintain absolute flow levels.

FIGS. 19A to 19C describe the adaptation of the heart pump 100A to heart chamber collapse. The example presented describes the consequences of left heart chamber collapse, however the opposite characteristics would occur for right heart chamber collapse. Furthermore, whilst this is described with respect to the heart pump 100A, the techniques are equally applicable to the heart pump 1 of FIGS. 1 to 5.

In the example of FIG. 19A, left heart chamber collapse impairs the flow of blood into the inlet 141 on left side of the heart pump, as shown at 47, resulting in a severe reduction of LVAD outflow from the outlet 151, as shown by the arrow 46a. As shown in FIG. 17D, an axial force vector toward the LVAD cavity ensues, which must be counteracted by an increase in bearing magnetic control flux, as shown by the arrow 43a, to thereby maintain the centralised impeller position.

However, the 'Zero Power' control method further automatically adjusts the impeller axial position toward the RVAD cavity 122A, as shown in FIG. 19B, until the bearing permanent magnet bias force shown by arrow 44b balances the disturbance hydraulic force 40. This action returns the electromagnetic control flux generated by the drive 170 and the bearing 180, as shown by the arrows 43b, 42b to minimal levels, thus reducing power consumption. Furthermore, RVAD outflow from the outlet 152 is increased and the pressure differential from LVAD inlet 141 to outlet 151 is decreased. This subsequently shifts blood into the pulmonary circuit, and consequently to the left heart chamber, thus alleviating the collapse of the left heart. LVAD and RVAD cavity pressures then return to a normal state, thus the disturbance force is eliminated, causing the impeller 130A to automatically translate back to the centre of the cavity 120, which in turn returns the balance of LVAD and RVAD outflows from the outlets 151, 152, as shown by the arrows 46c, 45c.

In another example, a single VAD heart pump, such as the heart pump 100B, is adapted to provide ventricular assistance to one side of a failing heart.

In this example, axial hydraulic force is imposed on the impeller 130B due to the build up of pressure within the first and second cavities 121, 122B. A differential of these pressures acting on the top and bottom impeller faces will produce a resultant force in either the positive or negative axial direction. The pressure differential arises due to flow between the inlet 141 and outlet 151, which can result in a pressure gradient across the face of the impeller 130B that includes the vanes, whereas the pressure gradient on the other face is substantially constant.

FIGS. 20A to 20D show the resultant axial force development on the impeller during a variety of common conditions. During diastole, as shown in FIG. 20A, the force beneath the impeller 130B is only partially balanced by the force acting on the top of the impeller, resulting in a net force towards the inlet 141, shown by the arrow 2000. This force decreases from the outer diameter to the inner diameter, in proportion to the pressure development along this path. This imbalance is reduced during systole, as shown in FIG. 20B, when the left ventricular pressure acts across the entire VAD impeller face.

The effect of an increase in systemic vascular resistance (SVR) on pressure development and thus force generation is described in FIG. 20C. Increasing SVR acts to increase the overall pressure in the pump cavity, which in turn increases the mismatch of force acting beneath and above the impeller 130B, resulting in a net force shown by arrow 2010, towards the inlet 141. Finally, the force generated on the impeller during instances of heart chamber collapse is described in FIG. 20D. In this instance, the pressure generated in the inlet cannula drops well below 0 mmHg, and the outlet correspondingly drops to a low value of pressure. This combination contributes to an increase in axial force toward the inlet 141, shown by the arrow 2020.

For the single heart support application, the two parameters in most need of control are the outflow pressure (and thus flow) in response to alterations in vascular resistance, and the rectification of heart collapse. The ability for the zero power controller to favourably adapt heart pump performance is described below for a number of foreseeable physiological conditions to be encountered by a single VAD.

Figure 21C:
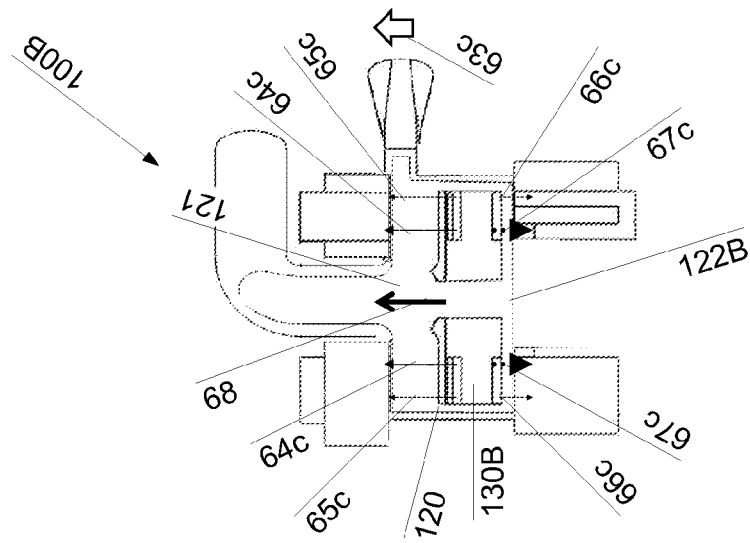
FIGS. 21A to 21C are schematic diagrams illustrating the adaptation of a VAD to alterations in relative vascular resistance; and, FIGS. 22A to 22C are schematic diagrams illustrating the adaptation of a VAD to heart chamber collapse.
Figure 21B:
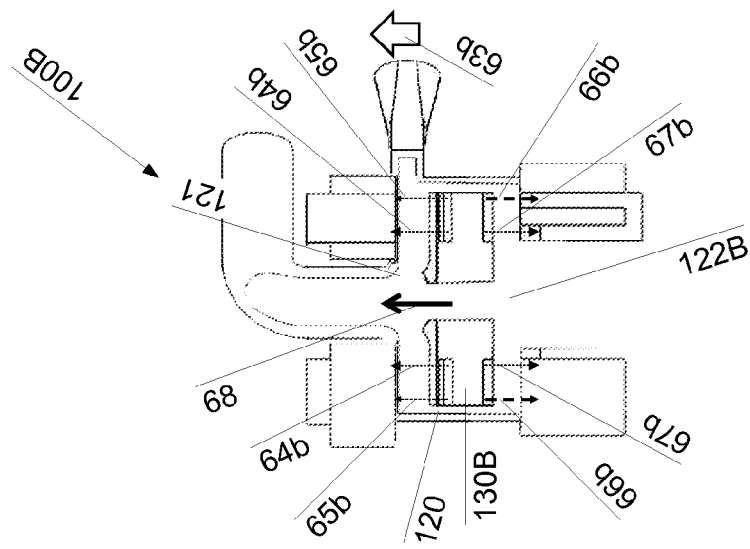
Figure 21A:
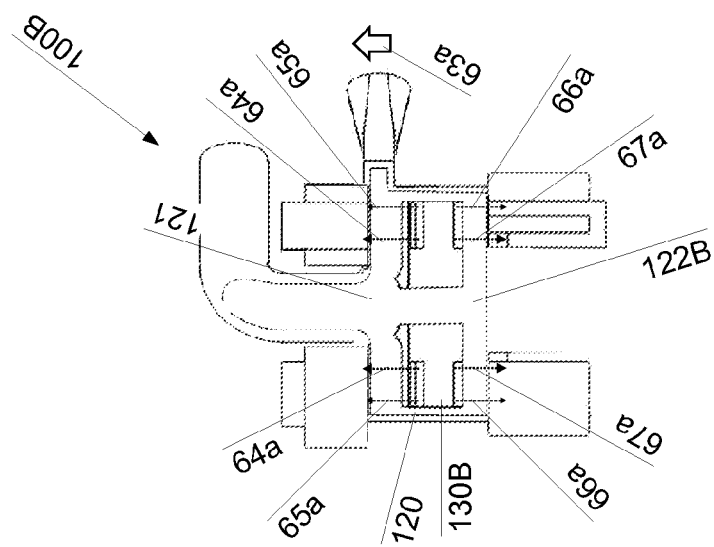

FIGS. 21A to 21C describe the adaptation of the heart pump 100B to increases in vascular resistance.

In FIG. 21A, during normal operation, the heart pump is configured so that with the impeller 130B positioned approximately centrally within the cavity 120, the outflow pressure and flow provided at the heart pump outlet 151 meets the circulation system's physiological requirements, as shown by the arrow 63a. In this configuration, with the impeller 130B located in the centre of the pump cavity 120, the bearing 180 and drive 170 PM bias forces shown by the arrows 67a, 64a, are in balance. Electromagnetic control flux from the drive 170 and the bearing 180 is minimal, as shown by the arrows 65a, 66a, and required only for stabilisation and to account for dynamic disturbances.

An increase in vascular resistance (VR), shown in FIG. 21B, causes an increase in VAD outlet pressure as shown by the arrow 63b and thus cavity pressure, which, as described in FIG. 20C, results in an increase of static axial hydraulic force toward the first cavity 121, as shown by the arrow 68. To maintain the impeller 130B in the central position, the magnetic bearing flux must increase in magnitude (and thus power), as shown by the arrow 66b, to thereby provide a restoring force.

However, in the single VAD application, this increase in outlet pressure due to the elevated VR should be reduced, as per the natural baroreceptor reflex. Alterations in flow can be achieved with speed changes, while flow balancing problems are negated by the ability for the remaining functioning ventricle's ability to balance the flow. Implementing the 'Zero power' controller as described above, will cause the impeller to move away from the first cavity 121 until the disturbance force 68 is balanced by the increase in PM bias flux from the bearing 180, as shown by the arrow 67c. In this equalised position, electromagnetic control flux is once again minimal, and required only for dynamic disturbance forces, thus power consumption is reduced. Most importantly however, VAD outflow pressure shown by the arrow 36c returns to a lower value, while outflow reduces (due to the increased vascular resistance). The opposite characteristic is observed for a decrease in vascular resistance (i.e. impeller movement toward the inlet), as encountered in a state of exercise. Thus the automatic impeller movement maintains vascular pressure, and thus outflow increases to suit.

Figure 22C:
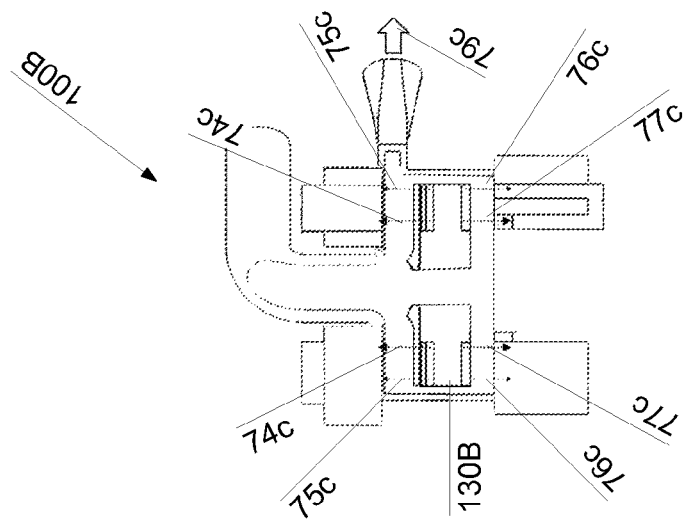
Figure 22B:
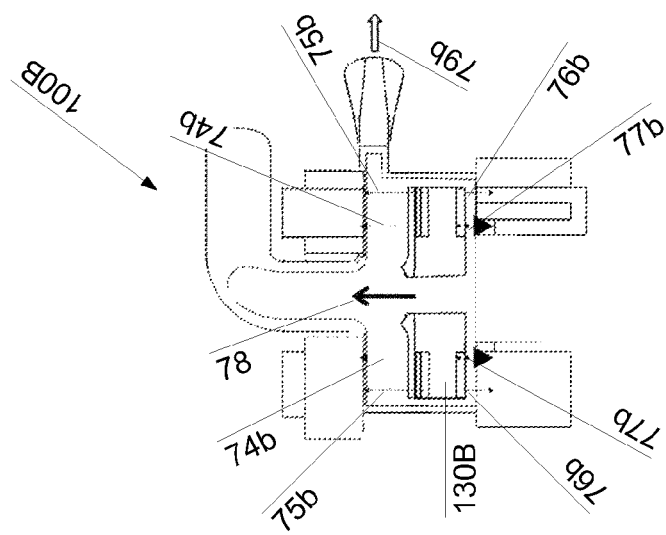
Figure 22A:
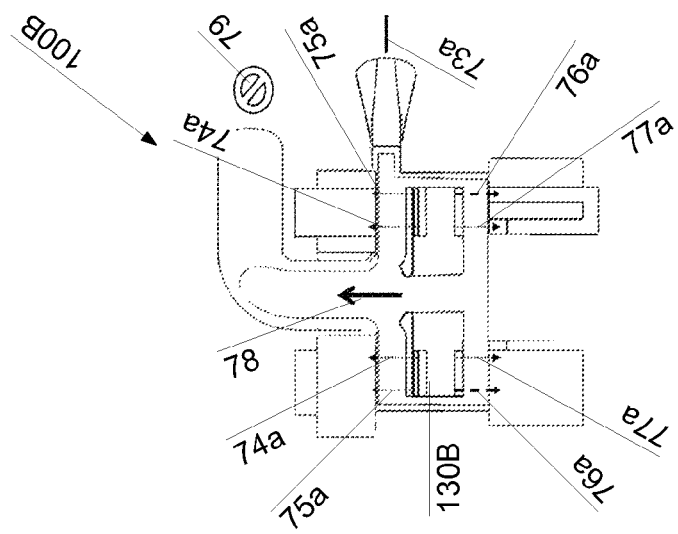
Figure 23A:
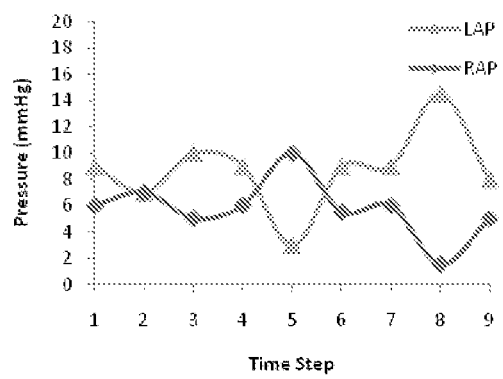
FIG. 23A is a graph of example left and right atrial pressures (LAP, RAP) for an example heart pump in a circulatory loop simulating a number of circulatory conditions.
Figure 23B:
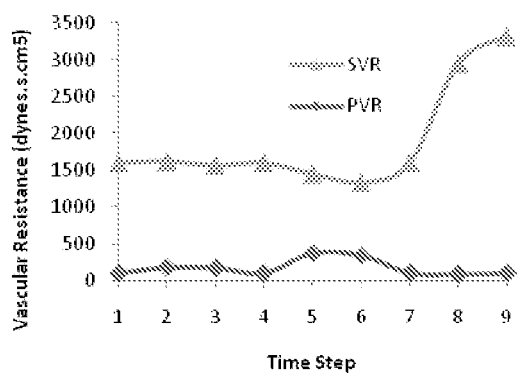
FIG. 23B is a graph of example systemic and pulmonary resistances (SVR, PVR) for an example heart pump in a circulatory loop simulating a number of circulatory conditions.
Figure 23C:
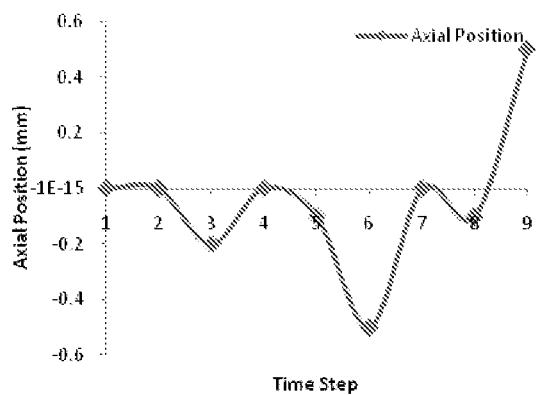
FIG. 23C is a graph of example impeller axial positions for an example heart pump in a circulatory loop simulating a number of circulatory conditions.
Figure 23D:
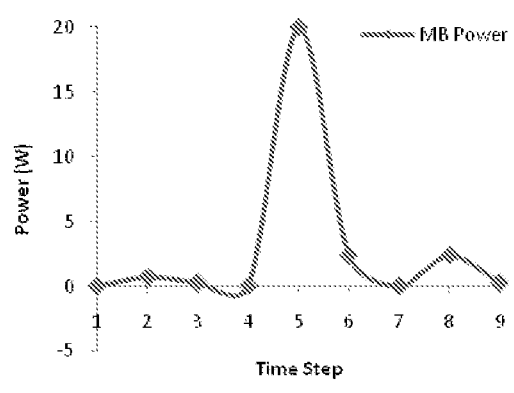
FIG. 23D is a graph of example magnetic bearing power (MB power) usage for an example heart pump in a circulatory loop simulating a number of circulatory conditions; and, FIG. 23E is a graph of example aortic and pulmonary pressures (AoP, PAP) for an example heart pump in a circulatory loop simulating a number of conditions.
Figure 23E:
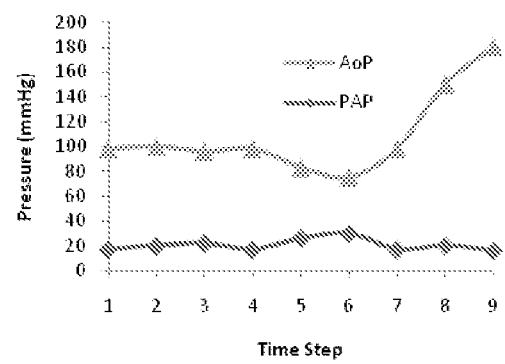

However, this increase in flow may lead to a situation of overpumping and thus heart chamber collapse. FIGS. 22A to 22C describe the adaptation of the heart pump 100B to this event.

When heart chamber collapse occurs, as shown in FIG. 22A, this impairs the flow of blood into the inlet 141, as shown by the arrow 79, resulting in a severe reduction of VAD outflow at the outlet 151, as shown by the arrow 73a. As described in FIG. 20D, an axial force vector toward the inlet 141 is developed, which must be counteracted by an increase in bearing magnetic control flux, shown by the arrow 76a, to maintain the centralised impeller position.

However, the 'Zero Power' control method automatically adjusts the impeller axial position away from the inlet cavity 141, until the bearing PM bias force shown by the arrow 77b balances the disturbance hydraulic force shown by the arrow 78, in FIG. 22B. This action returns the electromagnetic control fluxes shown by the arrows 75b, 76b to minimal levels, thus reducing power consumption. The pressure differential across the VAD inlet to outlet is therefore decreased, thus alleviating the collapse of the left heart. VAD cavity pressures then return to a normal state, eliminating the disturbance force and causing the impeller to automatically translate back to the centre of the cavity and returning outflow to normal, as shown by the arrow 79c in FIG. 22C.

Figure 9:
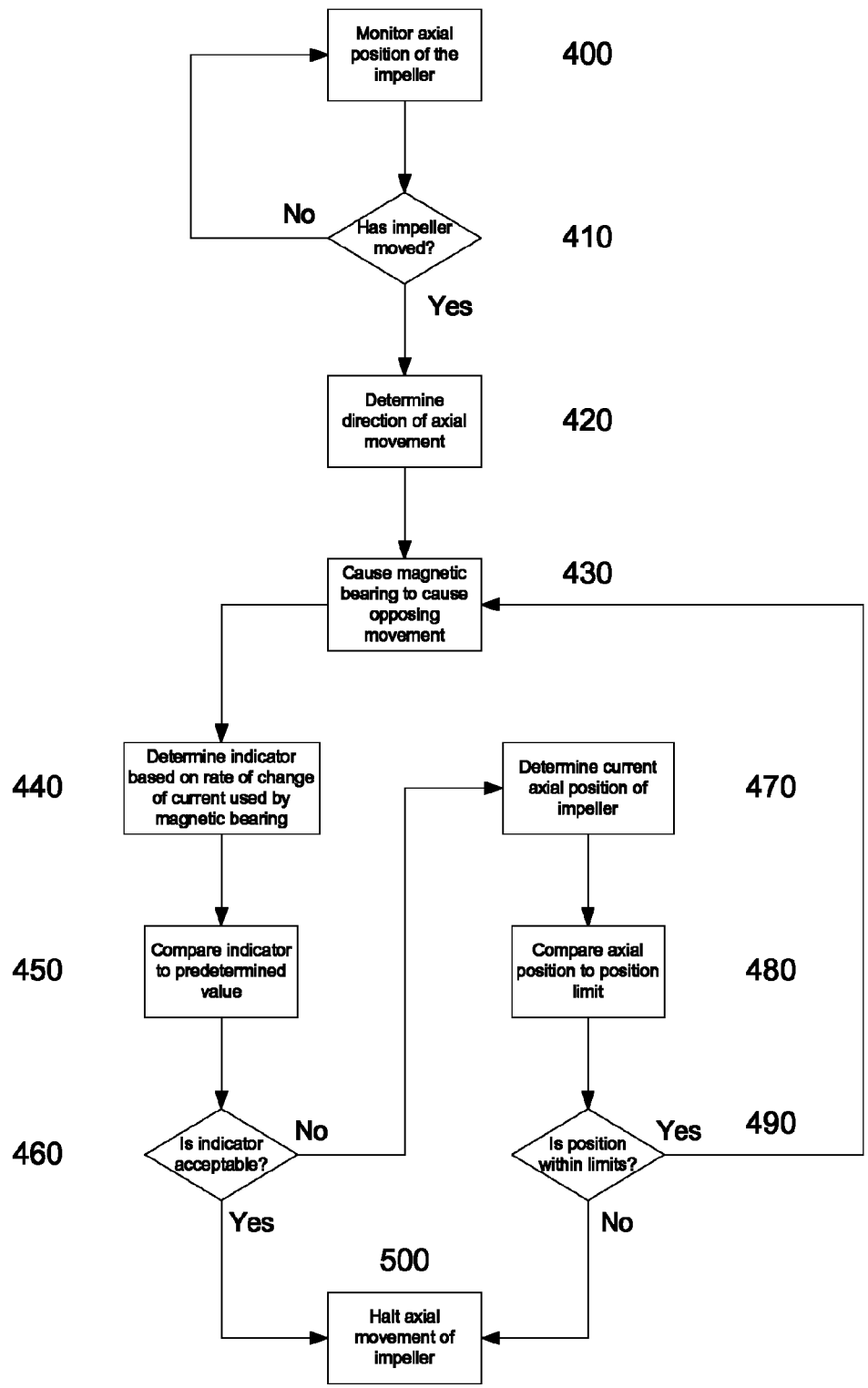
FIG. 9 is a flow chart of a second example of a method for controlling a position of an impeller in a heart pump.
Figure 10A:
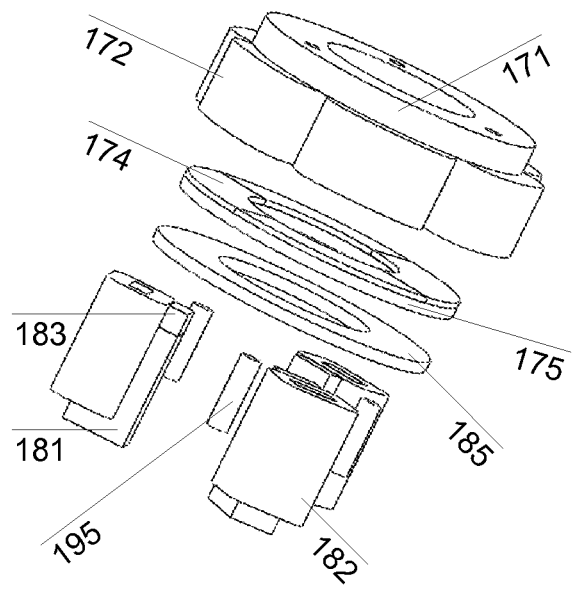
FIG. 10A is a schematic perspective exploded view of an example of drive and magnetic bearing system for a heart pump.
Figure 10B:
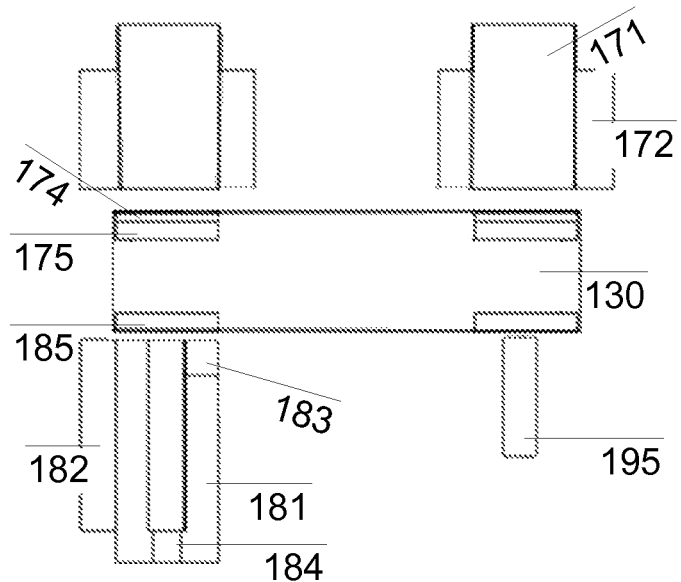
FIG. 10B is a schematic side view of the drive and magnetic bearing system of FIG. 10A.
Figure 10C:
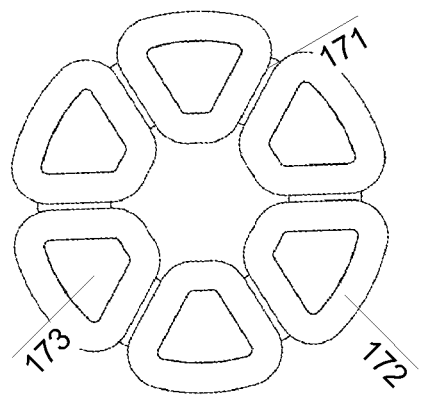
FIG. 10C is a schematic plan view of the drive system of FIG. 10A.
Figure 10D:
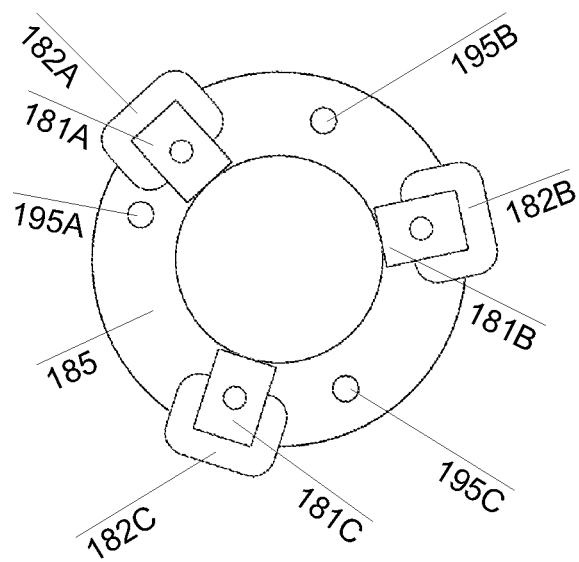
FIG. 10D is a schematic plan view of the magnetic bearing system of FIG. 10A.
Figure 10E:
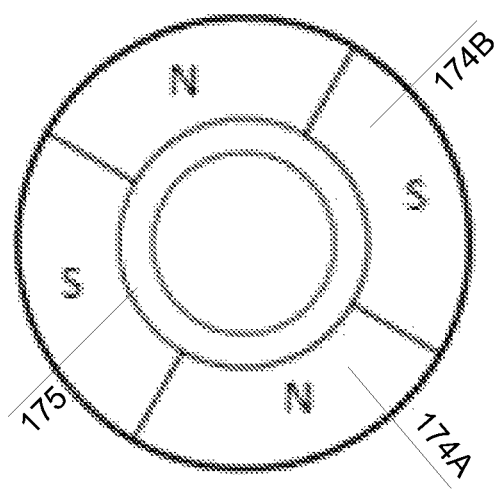
FIG. 10E is a schematic plan view of the rotor of the drive system of FIG. 10A.
Figure 10F:
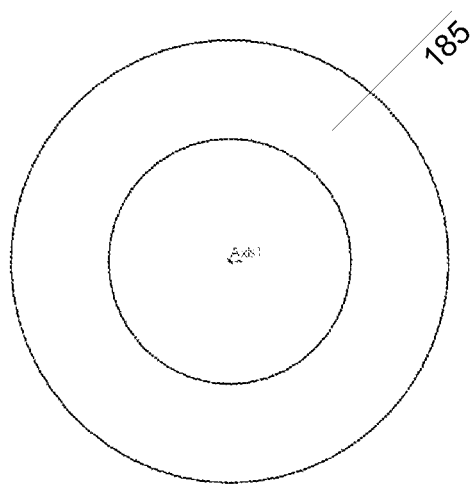
FIG. 10F is a schematic plan view of the rotor of the magnetic bearing system of FIG. 10A.

Experiments were performed using a heart pump similar to that shown in FIG. 6A, configured to operate in accordance with the control process of FIG. 9. The heart pump was coupled to a fluid circulation loop designed to simulate various hemodynamic conditions, such as Pulmonary Hypertension, LVAD inflow obstruction/left ventricular suckdown, and Systemic Hypertension, thereby allowing the responsiveness of the pump to be assessed.

All resulting parameters and haemodynamics are described in table 2, and illustrated in FIGS. 23A to 23E, with a detailed description provided subsequently. The conditions simulated can be summarised as follows:
1. Normal Condition (FIG. 12A)
2. Pulmonary Hypertension (FIG. 12B)
3. Impeller movement RIGHT to account for PHT (FIG. 12C)
4. Normal Condition
5. Suckdown event (19A)
6. Impeller movement RIGHT to account for Suckdown (19B)
7. Normal Condition (18A)
8. Systemic Hypertension (18B)
9. Impeller movement LEFT to account for SHT (18C)

TABLE 2

| Condition | 1 | 2 | 3 | 4 | 5 | 6 | 7 | 8 | 9 |
|---|---|---|---|---|---|---|---|---|---|
| Z* (mm) | 0 | 0 | −0.2 | 0 | −0.1 | −0.6 | 0 | −0.1 | 0.5 |
| AoP (mmHg) | 98 | 100 | 96 | 98 | 83 | 75 | 98 | 150 | 180 |
| PAP (mmHg) | 17 | 20 | 22 | 17 | 26 | 30 | 17 | 20 | 16 |
| LAP (mmHg) | 9 | 7 | 10 | 9 | 3 | 9 | 9 | 14.5 | 8 |
| RAP (mmHg) | 6 | 7 | 5 | 6 | 10 | 5.5 | 6 | 1.5 | 5 |
| SQ (L/min) | 5.1 | 5 | 5 | 5.1 | 4.6 | 4.4 | 5.1 | 4.2 | 4.5 |
| PQ (L/min) | 5.6 | 5.6 | 5.3 | 5.6 | 4.7 | 4.4 | 5.6 | 4.9 | 5.5 |
| SVR (dynes·s·cm$^5$) | 1600 | 1620 | 1565 | 1600 | 1450 | 1340 | 1600 | 2950 | 3320 |
| PVR (dynes·s·cm$^5$) | 94 | 168 | 163 | 94 | 370 | 340 | 94 | 78 | 91 |
| Hydraulic Force* (N) | 4.2 | 5 | 4.2 | 4.2 | 12 | 10.1 | 4.2 | 2.7 | 2.5 |
| Bearing Power (Watts) | 0 | 0.672 | 0.2625 | 0 | 20 | 2.3625 | 0 | 2.3625 | 0.2625 |

*Indicates a positive direction toward the LVAD cavity, Z = impeller axial position (mm), AoP = Aortic Pressure, PAP = Pulmonary Arterial Pressure, LAP = Left Atrial Pressure, RAP = Right Atrial Pressure, SQ = Systemic Flow Rate, PQ = Pulmonary Flow Rate, SVR = Systemic Vascular Resistance, PVR = Pulmonary Vascular Resistance.

In the first example, pulmonary hypertension was simulated. In practice, such an event occurring in the human body would result in a reduction of flow through the pulmonary system, thus reducing venous return to the left heart and a consequential increased potential for suck-down of the left heart chambers. An example of the response of the heart pump in such situations is as described above with respect to FIGS. 12A to 12C.

Referring to FIG. 12A, in an initial "normal" condition (Condition 1) the impeller 130A is positioned centrally with normal pressures and flows being produced at a rotational speed of 2500 rpm. This is achieved using an impeller 130A having a diameter of 50 mm in the first LVAD cavity 121 and approximately 25 mm in the second RVAD cavity 122A, with the vanes having a height of 1.4 mm, and a starting axial clearance gap of 0.5 mm, to thereby allow axial impeller movement of +/−0.5 mm.

In this case, the hydraulic force caused by the differential pressure from the RVAD and LVAD cavities 122, 121, respectively, equals +4.2N toward the LVAD cavity 121. This is immediately balanced by the magnetic bias force 187A caused by the permanent magnets within the magnetic bearing 180. Bearing current is only required for disturbance forces and thus the bearing electromagnetic force 186A and thus power usage equals zero, as shown in Table 2.

An incidence of Pulmonary Hypertension is then simulated (Condition 2), which is as described in FIG. 12B with results being illustrated in FIGS. 23A to 23E. The haemodynamic result is an immediate decrease in flow through the pulmonary system and left atrial pressure from 9 to 7 mmHg. In this case, the hydraulic forces F toward the LVAD/Motor are increased by 0.8N to +5.0N, due to the elevated pulmonary vascular resistance (168 dynes.s.cm$^5$). To maintain the impeller 130A in the central position, the controller 190 inputs current into the magnetic bearing 180 to produce an additional electromagnetic force 186B of 0.8N, thus balancing all external forces at the expense of an additional 0.672 W bearing power. If this condition remains, the reduced flow through the pulmonary system may further reduce left atrial pressure to induce suckdown in the left heart.

To avert this situation, the controller 190 then creates an "automatic response" condition (Condition 3) and FIG. 12C, whereby the impeller 130A is automatically moved toward the RVAD cavity −0.2 mm. In doing so, pulmonary arterial pressure increases as the RVAD improves its hydraulic efficiency, pushing more flow to the left heart to halt the reduction in left atrial pressure. This reduces the hydraulic force F on the impeller 130A by 0.8N, back to +4.2N. Motion of the impeller 130A towards the magnetic bearing 180 causes the magnetic bias force 187C created by the permanent magnets within the magnetic bearing 180 to increase in magnitude, to 5.3N. A small cancellation current of −0.25 amps is therefore required to pass through the bearing coils to reduce the bearing force to +4.2N and restore the force balance. This results in a bearing power of 0.26 W, which is less than the bearing power prior to movement (0.672 W) thus demonstrating the effect of the controller 190 to minimise bearing power when operating in a "zero power" mode as described above. These results highlight that the hemodynamic response of the pump functions as expected, and that the heart pump uses minimum power when in the automatic response state (Condition 3) required to counteract the pulmonary hypertension state.

In the second example, LVAD inflow obstruction was simulated. In practice, such an event occurring in the human body would result in a reduction of flow through the pulmonary system (due to increased PVR), and a consequential increased potential for suck-down of the left heart chambers. An example of the response of the heart pump in such situations is as described above with respect to FIGS. 19A to 19C.

The heart pump 100A and circulatory system are in an initial "normal" condition (Condition 4), which is substantially as for the normal condition (Condition 1) described above, and will not therefore be described in any further detail.

An incidence of left ventricular suckdown/obstruction is then simulated (Condition 5), as described in FIG. 19A. The haemodynamic result is an immediate decrease in left atrial pressure. In this case, the hydraulic forces 40 toward the LVAD/Motor are increased. To maintain the impeller in the central position, the controller inputs current into the magnetic bearing to produce an additional electromagnetic force (43a).

The controller 190 then seeks a minimal power position, which takes the impeller 130A in the direction of the RVAD cavity 122 by −0.1 mm. In this position, an electromagnetic force 43a of 12N is still required to balance all external forces, at the expense of 20 W of bearing power. As a result, the LAP reduces from 9 mmHg to 3 mmHg. If this condition remained, the reduced pulmonary flow may further reduce left atrial pressure to induce complete suckdown in the left heart.

The controller 190 then implements the automated response situation shown in FIG. 19B (Condition 6), by moving toward the RVAD cavity 122 to the position −0.5 mm, thereby minimising the power used by the magnetic bearing. In doing so, both aortic pressure and flow decrease as the LVAD reduces its hydraulic efficiency, whilst both pulmonary arterial pressure and flow increase as the RVAD improves its hydraulic efficiency, pushing more flow to the left heart to halt the reduction in left atrial pressure and raise it back to 9 mmHg and thus rectifying the suckdown event.

This motion decreases the force on the rotor by 1.9N (40) to +10.1N. The impeller motion toward the magnetic bearing causes the magnetic bias force 44b created by the permanent magnets within the magnetic bearing to increase in magnitude. A small cancellation current of −0.75 amps only is now required to pass through the bearing coils to reduce the bearing force to +10.1N and restore the force balance. This results in a bearing power of 2.36 W, which is less than the bearing power prior to movement (20 W) thus demonstrating the effect of the zero power controller to minimise bearing power.

A further slight motion back toward the LVAD cavity 121 would then fine tune the impellers operating position by increasing the permanent magnetic bias force and return a true zero power reading.

In a third example, systemic hypertension was simulated. In practice, such an event occurring in the human body would result in a reduction of flow through the systemic system, thus reducing venous return to the right heart and a consequential increased potential for suck-down of the right heart chambers. An example of this is shown in FIGS. 18A to 18C.

In FIG. 18A, the heart pump 100A and circulatory system are in an initial "normal" condition (Condition 7), which is substantially as for the normal condition (Condition 1) described above, and will not therefore be described in any further detail.

An incidence of Systemic Hypertension is then simulated (Condition 8), as shown in FIG. 18B. The haemodynamic result is an immediate decrease in right atrial pressure. In this case, the hydraulic forces toward the LVAD cavity 122 are decreased. Thus more electromagnetic power would be required by the magnetic bearing 180 to increase the magnetic bearing force 33b to maintain a set central impeller position.

In doing this, the impeller 130A may be allowed to move −0.1 mm toward the RVAD cavity 122. In this case, the hydraulic force toward the LVAD decreases by a further 1.5N to +2.7N, due to the excessively elevated systemic vascular resistance (2950 dynes.s.cm$^5$). To maintain the impeller 130A in this position, the controller inputs cancellation current into the magnetic bearing to reduce the bias electromagnetic force 34b by the required 1.5N, thus balancing all external forces at the expense of an additional 2.36 W bearing power. If this condition remained, the reduced LVAD outflow may further reduce right atrial pressure to induce suckdown in the right heart.

To avert this situation, the controller 190 then implements the automated response (Condition 9) as shown in FIG. 18C, whereby the impeller 130A is automatically moved toward the LVAD cavity 121 by +0.5 mm. In doing so, both aortic pressure and flow increase as the LVAD improves its hydraulic efficiency, pushing more flow to the right heart to halt the reduction in right atrial pressure. This decreases the hydraulic force on the rotor by an additional 0.2N (30), to +2.5N. The impeller motion toward the drive 170 causes the magnetic bias force 34c created by the permanent magnets within the magnetic bearing to decrease in magnitude. In this case, the total hydraulic force is almost balanced by the permanent magnetic bias force, needing only 0.26 W of magnetic bearing power to balance the force. Thus the magnetic bearing current 33c is essentially returned to a minimum, and thus a minimal power condition is observed.

The above described results highlight that the control process can therefore automatically adjust heart pump outflow in response to the conditions of the system in which it operates. In particular, the system uses an axial magnetic bearing and drive to suspend and rotate the impeller of the centrifugal blood pump, which is operated under a zero power control condition. This control process acts to automatically adjust the axial position of the impeller in response to changing axial hydraulic forces imposed on the impeller. This technique allows the heart pump to mimic the flow balancing property of the Frank-Starling law of the heart and thus automatically adapt to changes in atrial pressure (preload) and vascular resistance (afterload). This is particularly advantageous for preventing the potentially disastrous collapse of left or right heart chambers, as well as overcoming changes in vascular resistance.

One example application of the controller relates to its use in a Bi-ventricular assist heart pump. This heart pump includes an impeller having left and right vanes positioned on a shared rotating hub that is completely suspended in the blood. This suspension system incorporates an electromagnetic motor and axial magnetic bearing system for axial suspension and drive, while radial support is achieved using a hydrodynamic journal bearing. This journal bearing is well washed by the inherent shunt flow from left to right cavities. The left and right vanes have a different outer diameter to produce the pressure required of the systemic and pulmonary systems at a common rotational speed.

The instantaneous differential in flow required to balance outflow from the left and right hearts is achieved by the alteration of axial clearance above these semi-open vanes. Thus, an axial motion toward the left cavity will reduce the axial clearance gap above the left vane set, thus increasing the left heart outflow. Simultaneously, the gap above the right vane set will increase, thus reducing the right heart outflow. Similarly, a motion to the right cavity will induce the opposite effect.

This allows the heart pump to automatically adjust the outflow of the left and right cavities to minimise the potential for the left or right heart chambers to collapse, as well as to account for relative alterations in vascular resistance. For example, in the event of heart chamber collapse, the hub will translate away from the collapsed side, thus reducing the suction at the inlet whilst also increasing the flow from the opposite pump. When encountering an increase in relative vascular resistance, the impeller will translate toward the side with the increased afterload, thus enabling the affected side to overcome the resistance and maintain flow balance.

This enables a Frank Starling-like control of this flow balance, which is achieved automatically by the incorporation of the zero power magnetic control algorithm.

In another example application, the controller 190 is used for a single ventricular assist heart pump. This heart pump includes an impeller having a single set of vanes positioned on a rotating hub that is completely suspended in the blood. This suspension system again incorporates an electromagnetic motor and axial magnetic bearing system for axial suspension and drive, while radial support is achieved using a hydrodynamic journal bearing. This journal bearing is well washed by virtue of a hole in the impeller, which allows blood flow along an underside of the impeller.

Pressure control is achieved by the alteration of axial clearance above these semi-open vanes. Thus, an axial motion toward the inlet will reduce the axial clearance gap above the vanes, thus increasing the pressure developed in the pump.

This allows the heart pump to automatically adjust the pressure developed by the pump to minimise the potential of heart chamber collapse, as well as to account for pressure changes within the circulatory system. For example, in the event of heart chamber collapse, the hub will translate away from the inlet, thus reducing the suction at the inlet. When encountering an increase in vascular pressure, the impeller will translate away from the inlet, thus providing pressure relief.

Accordingly, the above described system can provide a VAD that can automatically control the outflow in response to the needs of the circulation system. This uses an axial magnetic bearing system that implements a zero power controller that adjusts the axial position of the impeller in response to hydraulic force. In one example, the motor and bearing arrangements each result in a net attractive force on the impeller 130, allowing the impeller to be provided at a balance point whose position is dependent on relative pressures in the pump cavity. By suitable arrangement, this can be used to provide relative flow control in BiVAD applications, and relative pressure control in VAD applications.

In one example, a combination of the axial movement (+/−0.3 mm) and small impeller blade heights (1-2 mm) produces sufficient change to outflow hydraulics at an unchanged rotational speed.

This can provide sensitivity to atrial (preload) pressure and arterial (afterload) pressure, as well as allowing rectification of heart chamber collapse. This allows the heart pump to maintain a suitable left/right flow balance, dependant on atrial pressure, in a BiVAD embodiment, or a set arterial pressure in a left or right VAD embodiment, similar to the baroreceptor reflex.

Accordingly, this avoids the need to change centrifugal pump rotational speed to produce changes in pump performance that is used in traditional heart pumps. This change in performance is advantageous to meet the physiological requirements of the circulatory system, whilst avoiding a complex and active physiological control algorithm that receives feedback from hardware sensors and uses software estimation to control pump speed. These hardware sensors induce further reliability issues that limit the long term durability of the heart pump, whilst the software estimation introduces complexity.

The control process also addresses the issue of flow balancing from the left and right pumps in a bi-ventricular assist system, particularly from a single rotary impeller system.

Accordingly, the control process provides a controller for a rotary type heart pump that can automatically and passively adjust the hydraulic output of its rotating impeller without changing rotational speed, and that does not rely on feedback from haemodynamic sensors or software estimation. Instead, the impeller alters its output in response to changes in preload and after load, similar to the Frank-Starling law of the heart.

In one example, the control process is achieved by the incorporation of an axial magnetic motor and bearing, which implements a zero power controller to automatically adjust the axial position of the centrifugal impeller within the pump cavity. The zero power controller responds to alterations in axial hydraulic force encountered when pump preload and afterload change. A change in performance with axial movement is most effectively observed when the impeller incorporates a set of semi open (unshrouded) blades.

The control process also provides the ability for a Bi-ventricular assist system to automatically adjust its flow rate in order to maintain a suitable left/right flow balance. This is most efficiently achieved in a solitary rotary type centrifugal heart pump implementing the 'zero power' controller and adapted to provide bi-ventricular assistance.

Persons skilled in the art will appreciate that numerous variations and modifications will become apparent. All such variations and modifications which become apparent to persons skilled in the art, should be considered to fall within the spirit and scope that the invention broadly appearing before described.

For example, functionality provided by separate motor and bearing arrangements could be achieved using a combined arrangement, in which one end of the housing includes a set of passive attractive magnets, whilst the other end of the housing includes a combined motor and bearing windings.

The claims defining the invention are as follows:

1. A heart pump including:
   a) first and second cavity portions, each cavity portion including a respective inlet and outlet;
   b) a connecting tube extending between the first and second cavity portion;
   c) an impeller including:
      i) a first set of vanes mounted on a first rotor in the first cavity portions;
      ii) a second set of vanes mounted on a second rotor in the second cavity portion; and,
      iii) a shaft connecting the first and second rotors, the shaft extending through the connecting tube;
      iv) a first magnetic material mounted in the first rotor; and
      v) a second magnetic material mounted in the second rotor;
   d) a drive for rotating the impeller, the drive being positioned adjacent the second cavity, the drive and second magnetic material being configured to result in an attractive force between the drive and the second rotor; and,
   e) a magnetic bearing including at least one bearing coil for controlling an axial position of the impeller, the magnetic bearing being positioned adjacent the first cavity, the magnetic bearing and first magnetic material being configured to result in an attractive force between the magnetic bearing and the first rotor; and wherein at least one of the drive and magnetic bearing being provided at least partially between the first and second cavity portions.

2. A heart pump according to claim 1, wherein the axial position determines a separation between each set of vanes and a respective cavity surface, the separation being used to control the fluid flows from the inlets to the outlets.

3. A heart pump according to claim 1, wherein the drive includes:
   a) the second magnetic material provided in the impeller; and
   b) at least one drive coil that in use generates a magnetic field that cooperates with the second magnetic material allowing the impeller to be rotated.

4. A heart pump according to claim 3, wherein the second magnetic material includes a number of circumferentially spaced permanent magnets mounted in the impeller, adjacent magnets having opposing polarities.

5. A heart pump according to claim 1, wherein, in use, the at least one bearing coil generates a magnetic field that cooperates with the first magnetic material in the impeller, allowing the axial position of the impeller to be controlled.

6. A heart pump according to claim 5, wherein the first magnetic material is a permanent magnet.

7. A heart pump according to claim 6, wherein the at least one bearing coil is for generating a magnetic field that is one of complementary to and counter to the first magnetic field generated by the permanent magnet, thereby controlling the net magnetic field between the bearing and the first magnetic material.

8. A heart pump according to claim 1, wherein the impeller includes:
   a) a second magnetic material provided on the second rotor for cooperating with the drive to allow rotation of the impeller; and,
   b) a first magnetic material provided on the first rotor for cooperating with the magnetic bearing to allow the axial position of the impeller to be controlled.

9. A heart pump according to claim 1, wherein:
   a) the magnetic bearing is positioned adjacent the first cavity, the magnetic bearing and first rotor being configured to result in a first attractive force between the magnetic bearing and the second rotor; and,
   b) the drive is positioned adjacent the second cavity, the drive and second rotor being configured to result in a second attractive force between the drive and the second rotor and wherein the first and second attractive forces are approximately balanced when the impeller is positioned at an approximately axially central position during normal circulatory conditions.

10. A heart pump according to claim 1, wherein the heart pump includes a controller for:
    a) determining movement of the impeller in a first axial direction;
    b) causing the magnetic bearing to move the impeller in a second axial direction opposite the first axial direction;
    c) determining an indicator indicative of the power used by the magnetic bearing; and,
    d) causing the magnetic bearing to control the axial position of the impeller in accordance with the indicator to thereby control a fluid flow between the inlets and the outlets.

11. A heart pump according to claim 10, wherein the controller is for:
    a) comparing the indicator to a threshold; and,
    b) causing the magnetic bearing to stop movement of the impeller in the second axial direction depending on the results of the comparison.

12. A heart pump according to claim 10, wherein the controller is for minimizing the power used by the magnetic bearing.

13. A heart pump according to claim 10, wherein the controller is for:
    a) comparing an axial position of the impeller to position limits; and,
    b) controlling the magnetic bearing to maintain the axial position of the impeller within the position limits.

14. A heart pump according to claim 10, wherein the controller is for:
    a) determining a pressure change within at least part of a cavity; and, b) controlling the axial position of the impeller in response to the pressure change.

15. A heart pump according to claim 14, wherein the controller is for determining the pressure change by detecting axial movement of the impeller.

16. A heart pump according to claim 10, wherein the controller is for:
   a) detecting movement of the impeller caused by a change in fluid pressure within at least one of the cavity portions; and,
   b) causing the magnetic bearing to control the axial position of the impeller to thereby change a fluid flow from the inlet to the outlet for at least one of the cavity portions.

17. A heart pump according to claim 16, wherein the controller is for, at least one of:
   a) causing the magnetic bearing to reduce the separation between the vanes and the cavity surface to thereby increase the flow of fluid from the inlet to the outlet; and,
   b) causing the magnetic bearing to increase the separation between the vanes and the cavity surface to thereby decrease the flow of fluid from the inlet to the outlet.

18. A heart pump according to claim 10, wherein the controller is for:
   a) detecting movement of the impeller caused by a change in relative fluid pressures in the cavity portions; and,
   b) causing the magnetic bearing to control the axial position of the impeller to thereby alter the relative flow of fluid from the inlets to the outlets.

19. A heart pump according to claim 10, wherein the controller is for:
   a) determining axial movement of the impeller away from a normal balance position;
   b) causing the magnetic bearing to move the impeller towards the normal position;
   c) monitoring the power used by the magnetic bearing;
   d) determining a new balance position in accordance with the power used by the magnetic bearing; and,
   e) causing the magnetic bearing to move the impeller to the new balance position.

20. A heart pump according to claim 19, wherein the normal balance position is used to maintain required fluid flows from each inlet to each outlet.

21. A heart pump according to claim 19, wherein the new balance position is offset from the normal balance position.

22. A heart pump according to claim 21, wherein the new balance position is used to adjust relative fluid flows between the inlets and the outlets.

23. A heart pump according to claim 10, wherein the indicator is determined using an indication of an electrical current used by the magnetic bearing.

24. A heart pump according to claim 23, wherein the controller is for determining a rate of change of current used by the magnetic bearing to cause axial movement of the impeller.

25. A heart pump according to claim 10, wherein the controller is for:
   a) determining movement of the impeller in a first axial direction;
   b) controlling the magnetic bearing to move the impeller in a second axial direction opposite the first axial direction until at least one of:
      i) the power used by the magnetic bearing falls below a predetermined amount; and,
      ii) the axial position of the impeller reaches a position limit.

26. A heart pump according to claim 10, wherein, the processing system includes:
   a) a memory for storing instructions; and,
   b) a processor that executes the instructions, thereby causing the processor to:
      i) determine movement of the impeller in the first axial direction;
      ii) generate a signal for causing the magnetic bearing to move the impeller in the second axial direction;
      iii) determine an indicator indicative of the power used by the magnetic bearing; and,
      iv) generate a signal for causing the magnetic bearing to control the axial position of the impeller in accordance with the indicator to thereby control a fluid flow between the inlet and the outlet.

27. A heart pump according to claim 1, wherein the heart pump includes a controller for:
   a) determining movement of an impeller from a balance position within a cavity, the cavity including at least one inlet and at least one outlet, and the impeller including vanes for urging fluid from the inlet to the outlet;
   b) causing a magnetic bearing to move the impeller to a new balance position based on an indication of power used by the magnetic bearing, the magnetic bearing including at least one coil for controlling an axial position of the impeller within the cavity, and the new balance position being used to control fluid flow from the inlet to the outlet.

28. A heart pump according to claim 1, wherein the heart pump includes a controller for controlling an axial position of an impeller within a cavity, a cavity including a first cavity portion having a first inlet and a first outlet and a second cavity portion having a second inlet and a second outlet, and the impeller including first and second sets of vanes, each set of vanes being for urging fluid from a respective inlet to a respective outlet, the controller controlling the axial position such that if the relative pressure in the first cavity increases relative to the second cavity, the impeller is positioned in the first cavity thereby increase the relative fluid flows from the first outlet relative to the second outlet.

29. A heart pump according to claim 1, wherein the heart pump includes a controller for controlling an axial position of an impeller within a cavity, a cavity including an inlet and an outlet, and the impeller including vanes for urging fluid from the inlet to the outlet, the controller controlling the axial position such that if the pressure in the cavity increases, the impeller is moves away from the inlet, thereby reducing an outlet flow pressure.

30. A method of controlling a heart pump, the heart pump including:
   a) first and second cavity portions, each cavity portion including a respective inlet and outlet;
   b) a connecting tube extending between the first and second cavity portion;
   c) an impeller including:
      i) a first set of vanes mounted on a first rotor in the first cavity portions;
      ii) a second set of vanes mounted on a second rotor in the second cavity portion; and,
      iii) a shaft connecting the first and second rotors, the shaft extending through the connecting tube;
   d) a drive for rotating the impeller; and,
   e) a magnetic bearing including at least one bearing coil for controlling an axial position of the impeller, at least one of the drive and magnetic bearing being provided at least partially between the first and second cavity portions, the method including:

i) determining movement of the impeller in a first axial direction;
ii) causing the magnetic bearing to move the impeller in a second axial direction opposite the first axial direction;
iii) determining an indicator indicative of the power used by the magnetic bearing; and,
iv) causing the magnetic bearing to control the axial position of the impeller in accordance with the indicator to thereby control a fluid flow between the inlets and the outlets.

31. A pump apparatus comprising:
a) a stator;
b) an upper rotor arranged spaced apart above the stator;
c) a lower rotor arranged spaced apart under the stator;
d) connecting means provided rotatably and vertically movable at the stator to connect the upper rotor and the lower rotor;
e) first electromagnetic means that is provided on one surface of the stator opposed to either one of permanent magnets, which are provided on a bottom surface of the upper rotor and a top surface of the lower rotor, cooperates with the permanent magnet, and that generates an acting force with respect to the rotor in an axial direction to thereby levitate the rotor;
f) second electromagnetic means that is provided on the other surface of the stator opposed to the other permanent magnet, and that cooperates with the permanent magnet to thereby rotationally drive the rotor;
g) first pumping means at which a first impeller provided on a top surface of the upper rotor rotates in a first pump chamber; and
h) second pumping means at which a second impeller provided on a bottom surface of the lower rotor rotates in a second pump chamber.

32. The pump apparatus according to claim 31, wherein the connecting means is composed of an axis of rotation inserted rotatably and vertically movable into a centre through-hole of the stator.

33. The pump apparatus according to claim 31, comprising a control section that moves the connecting means forward and backward in an axial direction and that can adjust a gap between the first impeller and an opposed surface of the first pump chamber, and a gap between the second impeller and the second pump chamber by coordinating them.

34. A heart pump including:
a) first and second cavity portions, each cavity portion including a respective inlet and outlet;
b) a connecting tube extending between the first and second cavity portion;
c) an impeller including:
i) a first set of vanes mounted on a first rotor in the first cavity portions;
ii) a second set of vanes mounted on a second rotor in the second cavity portion; and,
iii) a shaft connecting the first and second rotors, the shaft extending through the connecting tube;
iv) a first magnetic material mounted in the first rotor; and
v) a second magnetic material mounted in the second rotor;
d) a drive for rotating the impeller, the drive being positioned adjacent the second cavity, the drive and second magnetic material being configured to result in an attractive force between the drive and the second rotor; and,
a magnetic bearing including at least one bearing coil for controlling an axial position of the impeller, the magnetic bearing being positioned adjacent the first cavity, the magnetic bearing and first magnetic material being configured to result in an attractive force between the magnetic bearing and the first rotor.

* * * * *